(12) United States Patent
Scoglio et al.

(10) Patent No.: US 9,522,167 B2
(45) Date of Patent: Dec. 20, 2016

(54) ALPHANIZOMENON FLOS AQUAE PREPARATION, EXTRACTS AND PURIFIED COMPONENTS THEREOF FOR THE TREATMENT OF NEUROLOGICAL, NEURODEGENERATIVE AND MOOD DISORDERS

(75) Inventors: Stefano Scoglio, Urbino (IT); Franco Canestrari, Urbino (IT); Serena Benedetti, Urbino (IT); Yanina Benedetti, Urbino (IT); Maria Delgado-Esteban, Salamanca (ES)

(73) Assignee: Nutratec, s.r.l., Urbino (IT)

( * ) Notice: Subject to any disclaimer, the term of this patent is extended or adjusted under 35 U.S.C. 154(b) by 579 days.

(21) Appl. No.: 12/306,483

(22) PCT Filed: Jun. 26, 2007

(86) PCT No.: PCT/EP2007/005622
§ 371 (c)(1),
(2), (4) Date: Aug. 26, 2009

(87) PCT Pub. No.: WO2008/000430
PCT Pub. Date: Jan. 3, 2008

(65) Prior Publication Data
US 2009/0311286 A1 Dec. 17, 2009

Related U.S. Application Data

(60) Provisional application No. 60/816,593, filed on Jun. 27, 2006.

(51) Int. Cl.
*A61K 36/02* (2006.01)

(52) U.S. Cl.
CPC .................................. *A61K 36/02* (2013.01)

(58) Field of Classification Search
CPC .............................. A61K 36/02; A61K 35/748
USPC .................................................. 424/195.17
See application file for complete search history.

(56) References Cited

U.S. PATENT DOCUMENTS 5,455,276 A * 10/1995 Sabelli .......................... 514/655
7,651,690 B2 * 1/2010 Jensen et al. ............. 424/195.17
2005/0129709 A1 6/2005 Jensen et al.

FOREIGN PATENT DOCUMENTS

JP 58-065216 A 4/1983

OTHER PUBLICATIONS

Schaeffer (Ecotox. Environ. Safety (1999), vol. 44, pp. 73-80).*
http://www.mayoclinic.com/health/depression/DS00175/METHOD=print&DSECTION=all—accessed Feb. 2011.*
Ostensvik (Journal of Applied Microbiology (1998), vol. 84, pp. 1117-1124).*
"Reported Benefits of AFA (Aphanizomenon flos-aquae)" website (https://web.archive.org/web/20050303172330/http://www.bluegreenfoods.com/benefits.htm—internet archived version from Mar. 2005).*
http://www.ucsfhealth.org/conditions/neurological_disorders/—accessed Jun. 2015.*
Pugh, N. et al.; "Isolation of Three High Molecular Weight Polysaccharide Preparations with Potent Immunostimulatory Activity from Spirulina Platensis, Aphanizomenon Flos-Aquae and Chlorella Pyrenoidosa"; Planta Med; vol. 67; No. 8; 2001; pp. 737-742; New York.
Torres Avital et al.; "Porphyra-334, a potential natural source for UVA protective sunscreens"; Photochemical & Photobiological Sciences; vol. 5; No. 4; Apr. 2006; pp. 432-435.
Database WPI Week 198321; Derwent Publications Ltd., London, GB, AN-1983-50630K.
Benedetti et al., "Antioxidant properties of a novel phycocyanin extract from the blue-green alga Aphanizomenon flos-aquae", Life Sciences 75 (2004) 2353-2362.
Markesbery et al., "Oxidative Alterations in Alzheimer's Disease", Brain Pathology 9: 133-146 (1999).
Romay et al., "C-Phycocyanin: A Biliprotein with Antioxidant, Anti-Inflammatory and Neuroprotective Effects" Current Protein and Peptide Science, 2003, 4, 207-216.
Sabelli et al., "Sustained Antidepressant Effect of PEA Replacement", Journal of Neuropsychiatry, vol. 8, No. 2, pp. 168-171 (1996).
Ahmad et al., "Extraction, Separation and Identification of Chemical Ingredients of *Elephantopus scaber* L. Using Factorial Design of Experiment," International Journal of Chemistry, vol. 1, No. 1, pp. 36-49 (Feb. 2009).
Jensen et al., "Blue-Green Algae as an Immuno-Enhancer and Biomodulator," JANA vol. 3, No. 4, pp. 24-30 (2001).
Patterson et al., "Bioactive natural products from blue-green algae," Journal of Applied Phycology vol. 6, pp. 151-157 (1994).

* cited by examiner

*Primary Examiner* — Susan Hoffman
(74) *Attorney, Agent, or Firm* — Sherman D. Pernia

(57) ABSTRACT

The invention provides extracts of the microalga *Aphanizomenon Flos Aquae Aquae* Ralfs ex Born. & Flah. Var. *flos aquae* (AFA Klamath) and purified components thereof useful for the prevention or treatment of neurological, neurodegenerative and mood conditions or diseases.

6 Claims, 24 Drawing Sheets

ALPHANIZOMENON FLOS AQUAE PREPARATION, EXTRACTS AND PURIFIED COMPONENTS THEREOF FOR THE TREATMENT OF NEUROLOGICAL, NEURODEGENERATIVE AND MOOD DISORDERS

CROSS-REFERENCE TO RELATED APPLICATION

This application is a National Stage entry of International Application No. PCT/EP2007/005622, filed Jun. 26, 2007, which in turn claims priority from U.S. application No. 60/816,593, filed Jun. 27, 2006. The disclosures of the prior applications are hereby incorporated in their entirety by reference.

The present invention relates to the microalga *Aphanizomenon Flos Aquae Aquae* Ralfs ex Born. & Flah. Var. *flos aquae* (AFA Klamath). More precisely, the invention provides extracts of AFA Klamath and purified components thereof useful for the prevention or treatment of neurological, neurodegenerative and mood conditions or diseases.

BACKGROUND OF THE INVENTION

Phenylethylamine (PEA) is an endogenous amine synthesized by decarboxylation of phenylalanine in dopaminergic neurons of the nigrostriatal system, and may act as a neuromodulator of catecholamine neurotransmission in the brain (1). The most important action of PEA is promoting the neurotransmission of catecholamines. It is known that PEA stimulates the release of acetylcholine as well as dopamine (2). Furthermore PEA increases norepinephrine neurotransmission (NE) (6) and even serotonin neurotransmission.

Recently it has been shown that PEA can also work as an autonomous neurotransmitter, with its specific neuronal receptors; and that it acts as a true neuromodulator, being also able to depress neurotransmission if needed. (8)

From this derive a whole series of effects: stimulation of attention and memory; mood enhancement, with significant antidepressant activity; promotion of empathy and thus sociality, included emotional and sexual behavior; inhibition of hunger; reduction of the need for substance abuse and drug dependency.

The link between PEA and emotional mood has been confirmed by studies whereby significantly lower levels of PEA, measured as such or through its metabolite PAA (phenylacetic acid) in the plasma or urines, have been found in depressed subjects. (9)

It has been seen that Parkinson's patients have significantly lower levels of PEA, as measured directly in the plasma (12). The progressive reduction of neurotransmission, particularly dopaminergic, in these patients, is related to the progressive degeneration of the dopaminergic neurons of the substantia nigra.

This reduction in the PEA levels goes together with a parallel increase in levels of MAO-B in parkinsonian patients, hence the drugs used in Parkinson's are MAO-B inhibitors such as selegiline. (14) Moreover, once ingested PEA can easily pass through the blood-brain barrier and stimulate the release of dopamine from the nigrostriatal tissue even at low dosages. This is an important distinctive character, because the drug currently used, selegiline, while inhibiting MAO-B and the reuptake of dopamine, does not have any action on its release from the nigrostriatal tissue, and so it does not help to produce more dopamine, a serious limit in a pathology such as Parkinson, where the very generation of dopamine is greatly jeopardized.

Alzheimer's disease involves a degeneration of the mechanism of production and reuptake of dopamine and the progressive destruction of the neurons of the striatal area, which over time brings to a low number of dopaminergic neurons, and consequently of dopamine transmission. (15)

Although there are no clear data on the fact that ADHD (Attention Deficit Hyperactivity Disorder) is a neurodegenerative pathology, some studies have tried to prove that neuronal destruction is a main cause of ADHD in both children and adults. (19)

Most importantly there are evidences whereby the children affected by ADHD and learning disabilities have significantly lower levels of PEA (21), and so a reduction in the neuromodulation of attention (dopamine) and sedation (serotonine). That is why the drug of choice for ADHD is methylphenidate, a synthetic derivative of PEA, which also acts by stimulating a higher production of PEA (22), and thus of dopamine and norepinephrine, two neurotransmitters directly involved in the etiology of ADHD.

It is well known the use of amphetamines to control hunger and, consequently, weight. Their use in this area has always been controversial due to their side effects which, given also their tolerance, tend to become potentially very serious over time. This is confirmed by the fact that the main drugs currently used for hunger and weight control are amphetamine-like dopaminergic antidepressants, such as venlafaxine and buproprion. These molecules, as all amphetamines, are synthetic derivatives of PEA. The latter acts as a potent appetite suppressant insofar as its degradation by MAO-B enzymes is prevented.

Monoaminoxidase (MAO) A and B catalyze the degradation of neuroactive and vasoactive amines in the CNS and in peripheral tissues. MAO-B in particular, given its direct and indirect relevance to dopaminergic transmission, is involved in neurological disorders where dopamine is essential, such a depression and mood disorders, Parkinson and Alzheimer diseases. For this reason, MAO-B inhibitors are used in the treatment of such neurological disorders. (26)

DESCRIPTION OF THE INVENTION

The invention is based on the identification, in the microalga *Aphanizomenon Flos Aquae Aquae* Ralfs ex Born. & Flah. Var. *flos aquae* (AFA Klamath), of substances that, alone or in combination, exert beneficial effects on various neurological diseases, conditions, dysfunctions or disorders, including neurodegenerative diseases such as Alzheimer's and Parkinson's, multiple sclerosis, hyperactivity and attention deficit disorders (ADHD), autism, depression, memory deficit and mood disturbances. In particular, it has been found that AFA Klamath microalga contains, besides phenylethylamine, which is a neuromodulator characterized by dopaminergic and noradrenergic activity, specific molecules which quite surprisingly proved to be very effective inhibitors of the enzyme monoaminoxidase B (MAO-B), namely: a) the specific AFA-phytochrome; b) the AFA-phycobiliprotein complex containing a phycobilisome formed by C-phycocyanin (C-PC) and phycoerythrocyanin (PEC, including its chromophore phycoviolobilin or PVB) ("AFA-phycocyanins"); c) mycosporine-like amino acids or MAAs. This finding is very important since the PEA contained in the algae, unless protected by MAO-B inhibitors, would be rapidly destroyed upon ingestion by the MAO-B enzyme.

The same molecules that act as MAO-B selective inhibitors, also perform a powerful neuroprotectant role, thus significantly enhancing the ability of the extract to promote neurological health.

Accordingly the invention provides a method for preventing, controlling or treating the above mentioned neurological diseases, conditions, dysfunctions or disorders by administering to a subject in need thereof an AFA Klamath preparation, particularly an extract enriched in such active components, or an isolated and purified component selected from: a) the AFA phytochrome, b) the C-phycocyanin/phycoerythrocyanins complex, as present in AFA or in any other microalgae; c) the mycosporine-like amino acids *porphyra* and shinorine, as present in AFA or from any other algal source; d) or a mixture thereof.

Preferably the AFA Klamath extract according to the invention is prepared by the following steps:
  a) freezing the freshly harvested AFA alga and thawing it, or, if the starting material is dried AFA powder, sonicating the water-diluted AFA powder to disrupt the cells;
  b) centrifuging the product of step a) to separate the supernatant (retaining most of the cytoplasmatic portion) from the precipitate (retaining most of the cell wall fraction);
  c) collecting the supernatant containing the water-soluble components.

The resulting product is an extract (indicated as "Basic Extract") which concentrates PEA as well as other synergic molecules such as the AFA phytochrome, the AFA-phycocyanins, and the MAAs. For example, whereas Klamath microalga has a natural content of PEA ranging from 2 to 4 mg/gr, the Basic Extract increases this concentration to a level ranging from 9 to 11 mg/gr (HPLC analysis).

It is possible to further purify the extract by passing it through ultra-filtration system, preferably through a membrane with a molecular weight cut-off of 30.000 Daltons. The ultra-filtration retentate (Extract A) contains as major active components both the AFA-phycocyanins (mol. weight=121.000) and the AFA-phytochrome (mol. Weight 480.000). Interestingly, even though MAAs have a molecular weight well below the cut-off size employed, the retentate also increases the concentration of MAAs.

The Basic Extract obtained by steps a) to c), i.e. without ultra-filtration, is generally preferred as it contains the most appropriate amounts of PEA, AFA-phytochrome, AFA-PC and MAAs. Moreover, this Basic Extract also includes substances such as chlorophyll and carotenes, even though in a reduced proportion, contributing to its antioxidant and anti-inflammatory properties.

In alternative, the active components of AFA Klamath, namely the complex C-phycocyanin/phycoerythrocyanins (C-PC/PEC), AFA phytochrome and MAAs can be isolated and purified, as further described below, and used in a method according to the invention.

In a preferred embodiment, AFA Klamath C-PC/PEC complex, AFA's phytochrome and mycosporine-like amino acids are used as a combined preparation for simultaneous or separate administration to a subject in need thereof; in a yet further preferred embodiment, such a combined preparation contains phenylethylamine as an additional active ingredient. Among the mycosporine-like amino acids, shinorine and *porphyra*-334 are particularly preferred, as they are contained in relatively higher concentration in AFA Klamath microalgae.

The observed inhibition of monoaminoxidase-B is particularly relevant as it allows to increase dopaminergic transmission and minimize the catabolism of PEA. Significantly, both phytochrome and AFA-phycocyanin inhibit MAO-B in a reversible and mixed way, whereas MAO-B inhibition by MAAs is competitive and reversible; therefore, all three molecules assure high efficacy in physiological conditions and in the absence of side-effects.

In a further aspect, the invention is directed to a nutraceutical or pharmaceutical composition containing an AFA Klamath preparation, an extract or an isolated component thereof which is preferably selected from the C-PC/PEC complex, as present in AFA or from any other microalgal source, or the isolated C-PC and PEC single components; AFA phytochrome; the mycosporine-like amino acids *porphyra* and shinorine, as present in AFA algae or from any other algal source; or mixtures thereof; with the optional addition of phenylethylamine. In a preferred embodiment, the nutritional compositions are dietary supplements in the form of tablets, capsules, beverages; in a further preferred embodiment the pharmaceutical compositions are in the form of tablets, capsules, sachets, syrups, suppositories, vials and ointments and can be used for the prevention or treatment of neurological or neurodegenerative diseases or conditions indicated above. The AFA Klamath liquid extracts according to the invention can be either used as such or can be dried through methodologies such as freeze-drying, spray-drying or the like. The isolated active components can be formulated using techniques and following procedures that are known to anyone skilled in the art.

The dose of active ingredient will depend on the intended use of the compositions, whether as nutritional supplement or as a pharmaceutical preparation. The effective amount of each component will be generally comprised in the following ranges: PEA=0.1-100 mg, preferably 5-30 mg; phytochrome=0.1-1000 mg, preferably 0.8-10 mg; MAAs=0.1-1000 mg, preferably 10-100; phycocyanins=1-2500 mg, preferably 50-1000 mg.

DETAILED DESCRIPTION OF THE INVENTION

Identification of "AFA-Phytochrome", a Unique Phytochrome Typical of Klamath Algae Phytochromes are photoreceptors, pigments that plants use to detect light and that are sensitive to light in the red and far-red region of the visible spectrum. They perform many different functions in plants, including the regulation of flowering (through circadian rhythms), germination and the synthesis of chlorophyll. The latter is particularly relevant in relation to AFA algae, because the presence of this unique type of phytochrome in AFA may be explained by its lack of the other phycobiliprotein commonly used by other cyanobacteria to complement C-phycocyanin in the process of photosynthesis, namely allo-phycocyanin. While the place of allo-phycocyanin in Klamath algae is taken by phycoerythrocyanin or PEC (see below), it is likely that PEC alone is not sufficient, especially considering that Klamath algae lives in a non-tropical environment which needs a high light harvesting efficiency, and so AFA algae seem to integrate their higher needs with the phytochrome.

The AFA phytochrome which has a peculiar structure, is described here for the first time. Over the years, different types of phytochromes have been found in plants, which not only have different phytochrome genes (3 in rice and 6 in maize, for instance), but in most cases they have significantly different protein components and structure. What makes them all phycochromes is that they all use the same biliprotein, called phytochromobilin, as a light-absorbing chromophore. This chromophore is similar to the phycocyanin's chromophore phycocyanobilin, and is characterized by a single bilin molecule consisting of an open chain of four pyrrole rings (tetrapyrroles). More specifically, in its $P_r$ normal state this biliprotein absorbs light at a maximum of 650-670 nM, whereas when activated by red light it is transformed into $P_{fr}$ with an absorbance maximum of 730 nM.

The first cyanobacterial phytochrome to be discovered, that of *Synechocystis*, showed to have a weak structural similarity with plant phytochromes. Nevertheless, *Synechocystis*'s biliprotein is generally considered a phytochrome insofar as it is a red/far-red reversible chromoprotein. (48)

AFA Phytochrome Purification and Characterization

AFA-phytochrome has a biliprotein as its chromophore that absorbs light in the red/far-red spectrum. To establish its structure and activities we have purified the phytochrome with the following protocol:

Suspend 1 g of extract in 10 ml of 1 K-phosphate buffer, pH 7.0

Vortex twice for 1 min with half their volume

Incubate cells for 35' with 2% Triton X 100

Centrifuge at 28000 rpm for 16-18 h

Collect supernatant on a sucrose density step gradient

Spin the gradient using swing-out rotors at 150000 g for 12 h

Store at −20° C.

Figure 22:
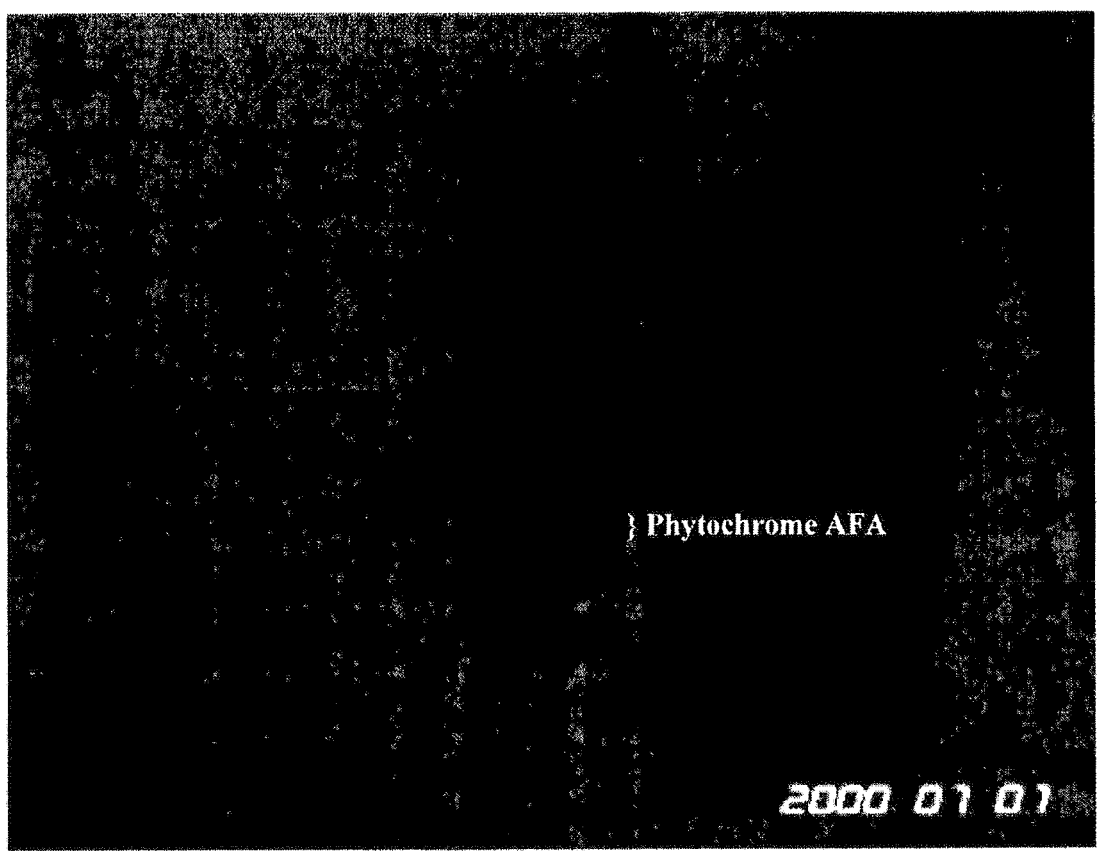
FIG. 22 shows the relation of the AFA-phytochrome band and the phycobilisome bands and gives an indication of the molecular weight of the AFA-phytochrome present in algae.

The phytochrome corresponds to the lysate band of an intense orange color, which is visible at approximately 1M of sucrose, while the phycobilisome stands at approximately 0.75 M. This relation of the two bands also gives a reliable indication about the molecular weight of the phytochrome present in the algae, which is about 4 times that of the trimeric AFA-PC: the latter being 121 Kd, we can preliminarily establish the MW of AFA-phytochrome at approximately 480 Kd (FIG. 22)

Figure 23:
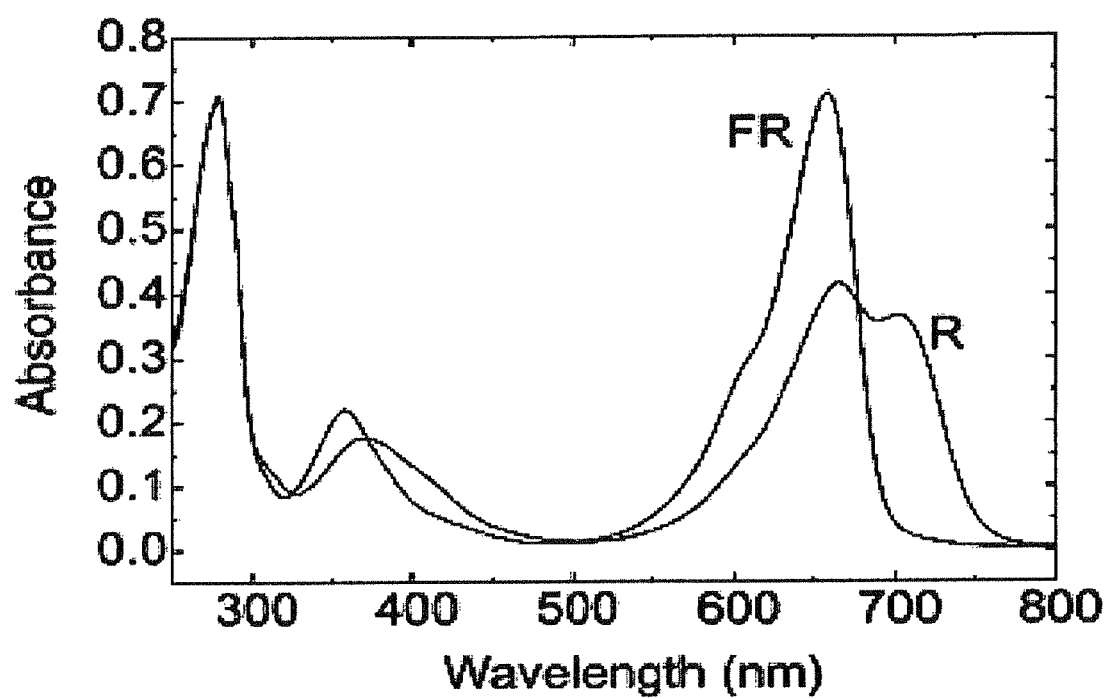
FIG. 23 shows the light absorption properties of the AFA-phytochrome at 672 nm and 694nm, which corresponds respectively to red-absorbing and far-red absorbing forms in a state of equilibrium.

Tested for its light-absorbing properties, the phytochrome shows to absorb light with two peaks at 672 nM and 694 nM, which corresponds respectively to $P_r$ (red-light absorbing) e $P_{fr}$ (far-red light absorbing) forms in a state of equilibrium (FIG. 23).

As to the quantity of phytochrome contained in AFA, our first evaluation gives the following preliminary result: 2 mg/gr (or 0.2% DW). As to the extracts, the concentration increases to approximately 0.5% in the Basic Extract, and approx. 1% in the Extract B. These are low concentrations, yet the antioxidant/antinflammatory potency of this molecule is so strong that even a very small quantity can produce very relevant effects.

Antioxidant Activity

Figure 24:
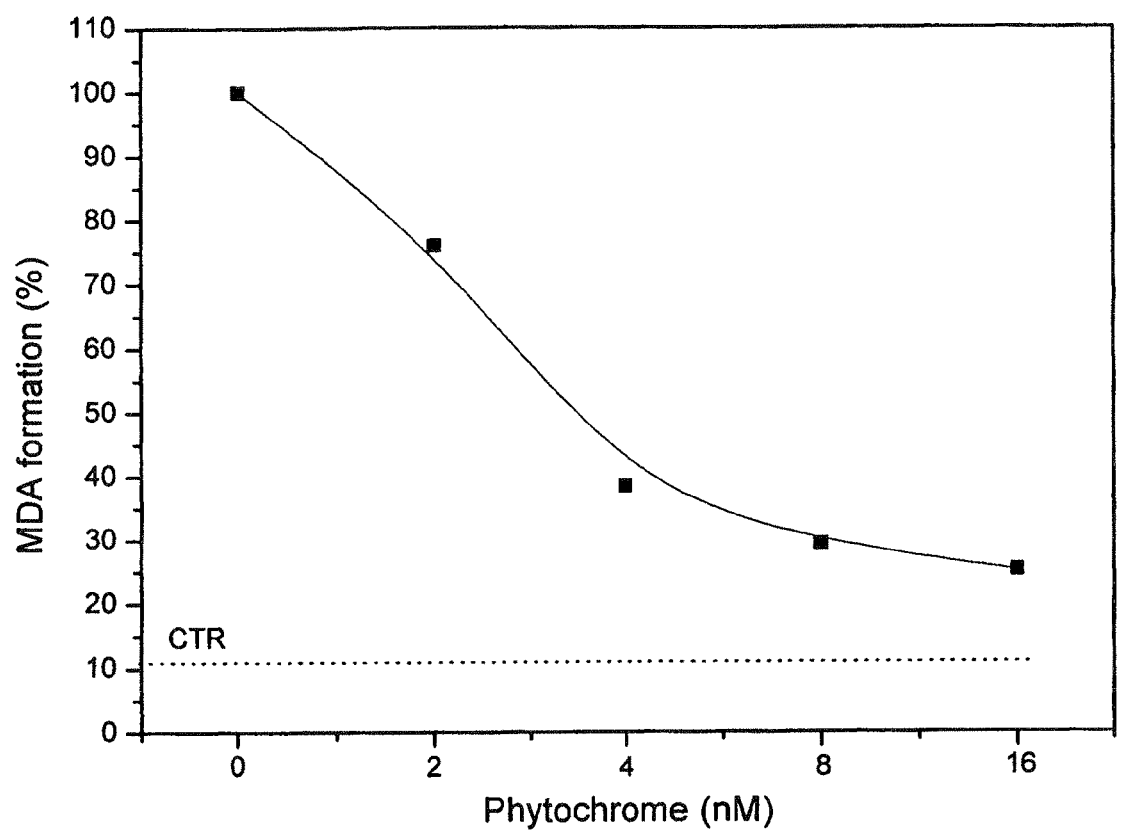
FIG. 24 shows that % MDA formation of AFA-phytochrome after incubation with plasma.

The purified AFA-phytochrome has shown to be a very powerful antioxidant. In fact, in absolute terms, the most powerful molecule so far found in Klamath algae. The incubation for 2 hrs. of human plasma samples with oxidative agent $CuCl_2$ at 100 μM generates increased levels of malondialdehyde (MDA), a late byproduct of lipid peroxidation which is measured through spectrophotometer at 535 nm after a reaction with thiobarbituric acid (TBA test). When plasma is incubated for 2 hrs at 37° C. with $CuCl_2$ 100 μM together with increasing quantities of AFA-phytochrome (2-16 nM) extracted from AFA algae, a very strong dose-dependent reduction of the MDA levels is observed (FIG. 24). In fact, an almost complete inhibition of lipoperoxidation is obtained with MDA levels close to control, with just 16 nM of AFA phytochrome. Significantly, the IC50 of 3.6 nM is 45 times less than that obtained for the PCB. The phytochrome is the main responsible for the antioxidant and neuroprotecting effects of the Basic Extract, which are higher than those of AFA-PC.

Extraction, Purification and Quantification of MAAs

We tested the presence of MAAs in the cyanophyta *Aphanizomenon flos-aquae* of Klamath Lake, generally known as Klamath algae. To our knowledge, only a very recent report exist on the occurrence of MAAs in any *Aphanizomenon* species (47); however, such report only identifies *porphyra* as the MAAs present, whereas our research shows the presence of two MAAs, both *porphyra* and shinorine. On the other hand, in relation to the overall literature on algae, whereas most of the cyanobacteria reported to date contain shinorine as their primary MAAs, we found a rare occurrence of *porphyra*-334 as the primary MAA in *Aphanizomenon flos-aquae* in addition to shinorine.

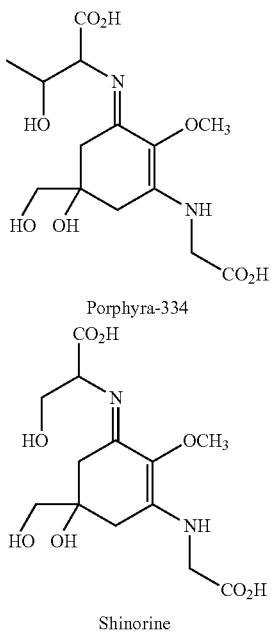

Porphyra-334

Shinorine

MAAs were extracted as previously reported. (29) Briefly, 20 mg of AFA powder or 20 mg. of aqueous extract are extracted in 2 ml of 20% (v/v) aqueous methanol (HPLC grade) by incubating in a water bath at 45° C. for 2.5 h. After centrifugation (5000 g; GS-15R Centrifuge, Beckman, Palo Alto, USA), the supernatant was evaporated to dryness and re-dissolved in 2 ml 100% methanol, vortexed for 2-3 min and centrifuged at 10000 g for 10 min. The supernatant was evaporated and the extract re-dissolved in the same volume of 0.2% acetic acid for the analysis in HPLC or in 200 µl of phosphate buffer (PBS) for the evaluation of antioxidant properties. The samples were filtered through 0.2 µm pore-sized syringe filters (VWR International, Milan, Italy) before being subjected to HPLC analysis, or to the test of antioxidant properties (see below).

The MAAs of Klamath algae have an absorption maximum of 334 nm. Further purification of MAAs was done using a HPLC system (Jasco Corporation, Tokyo, Japan) equipped with a Alltima C18 column and guard (4.6×250 mm i.d., 5 µm packing, Alltech, Milan, Italy), according to the literature (30). The wavelength for detection was 330 nm; the mobile phase was 0.2% acetic acid at a flow-rate of 1.0 ml min$^{-1}$. Identification of MAAs was done by comparing the absorption spectra and retentions time with standards such as *Porphyra* and *Pterocladia* sp., mainly containing *porphyra*-334, shinorine and palythine, kindly provided by Dr Manfred Klisch, Friedrich-Alexander-Universitat, Erlangen, Germany. Absorption spectra of samples were measured from 200 to 800 nm in a single-beam spectrophotometer (DU 640, Beckman, Palo Alto, USA). The raw spectra were transferred to a computer and treated mathematically for the peak analyses of MAAs.

Figure 1:
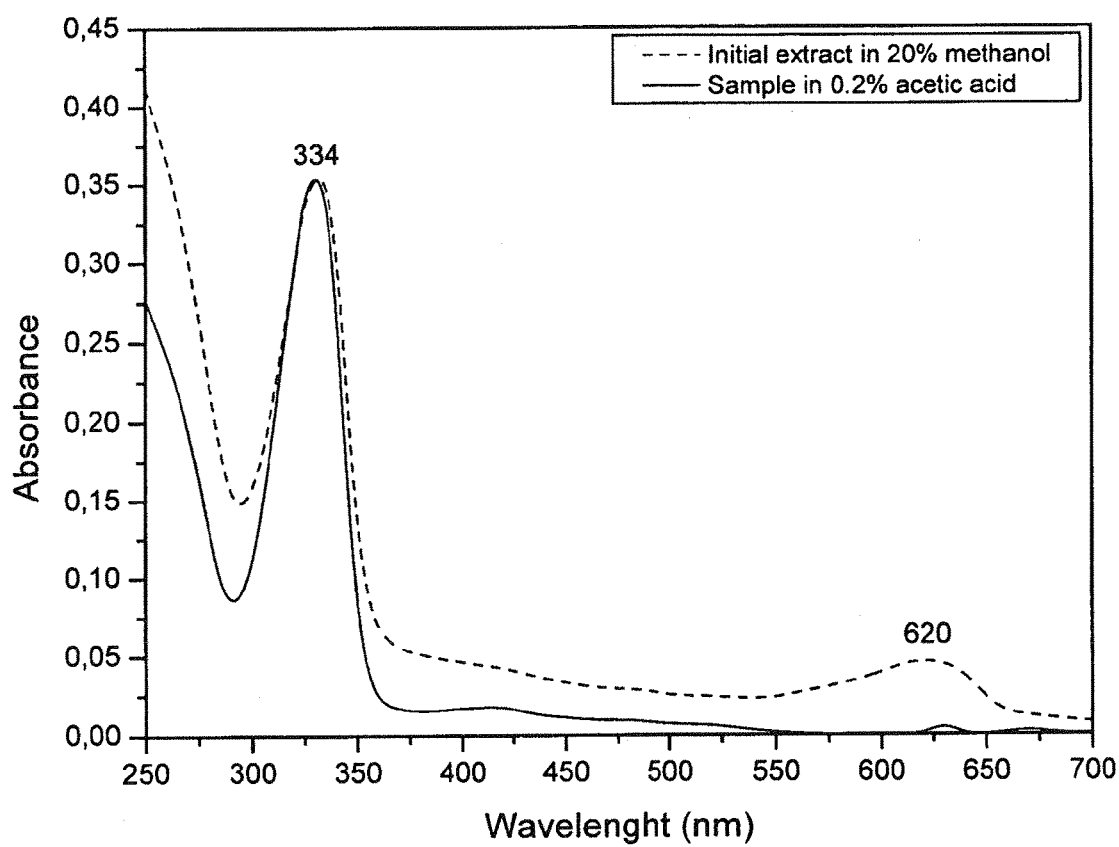
FIG. 1 shows the absorption of partially purified mycosporine-like amino acids (MAAs) from an AFA sample.

MAAs were partially purified from AFA sample and from the aqueous extract as described earlier. Extraction of samples with 20% methanol at 45° C. for 2.5 h resulted in a prominent peak at 334 nm (MAAs); even if small amounts of photosynthetic pigments (such as phycocyanin at 620 nm) were also extracted with this procedure (see FIG. 1, dashed line). MAA samples were further treated with 100% methanol in order to remove proteins and salts and finally with 0.2% acetic acid to remove non polar-photosynthetic pigments. The resultant partially purified MAAs had an absorption maximum at 334 nm (FIG. 1, solid line).

Figure 2:
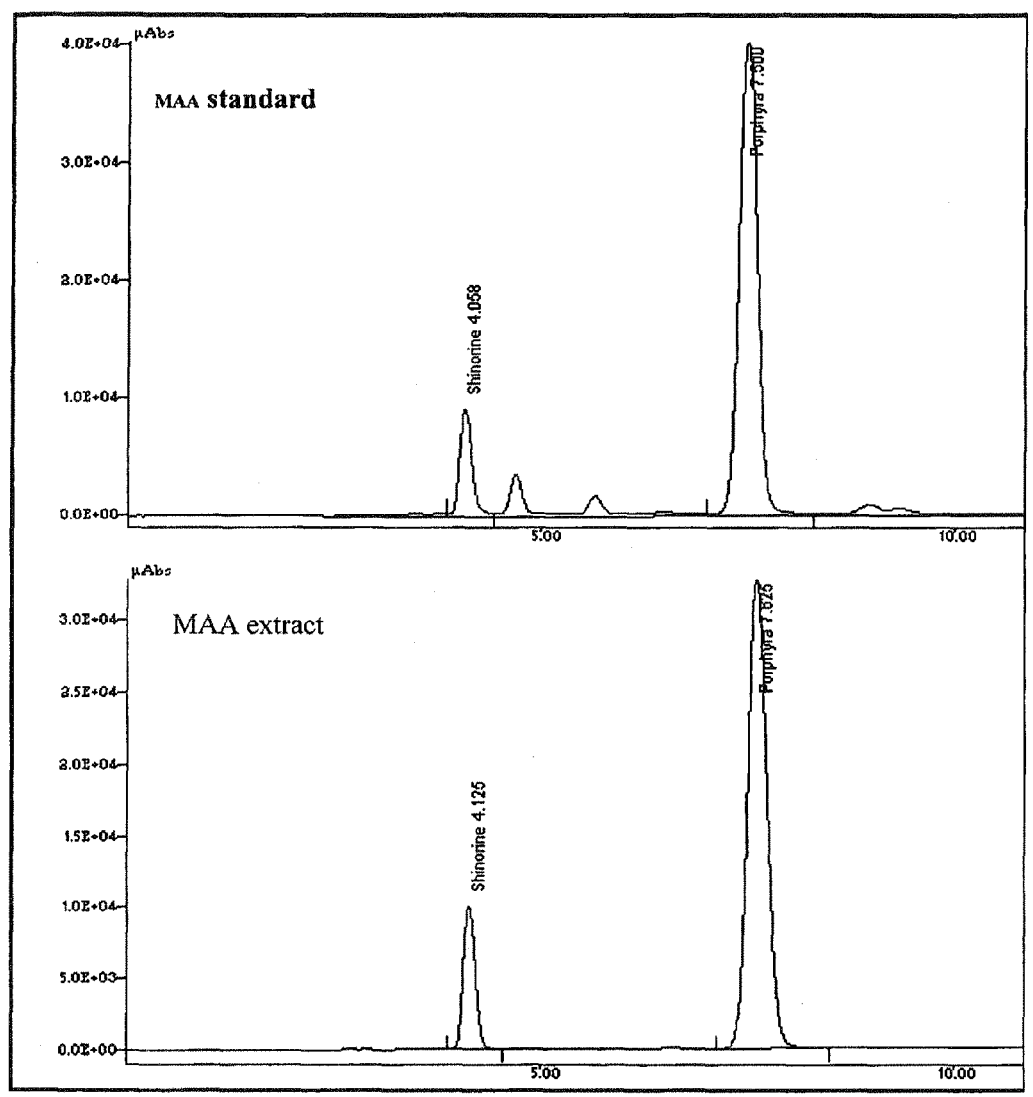
FIG. 2 shows chromatograms from partially purified AFA samples.

Further analysis and purification of MAAs was done by HPLC with a view to find whether the compounds absorbing at 334 nm was a single MAA or a mixture of more than one MAAs. The chromatogram of the sample (FIG. 2) shows the presence of two MAAs with retention times of 4.2 (peak 1) and 7.6 min (peak 2) that were identified as shinorine and *porphyra*-334, respectively. *Porphyra*-334 seems to be the major MAA in AFA since shinorine was present only in small quantities (peak area ratio 1:15).

Figure 3:
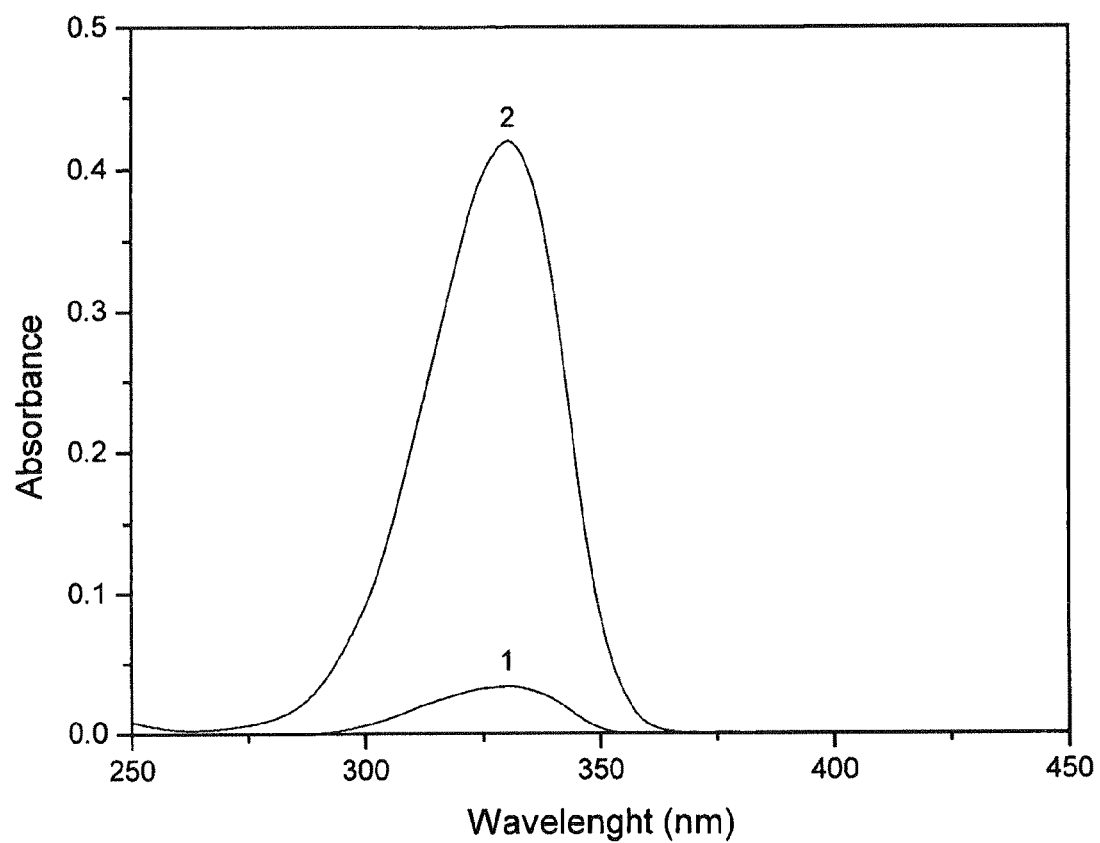
FIG. 3 shows UV spectra of purified MAAs.

The UV spectra of the purified MAAs confirmed their absorption maximum at 334 nm (FIG. 3).

Taking into account that the molar extinction coefficients at 334 nm for shinorine and *porphyra*-334 are of 44700 and 42300 M$^{-1}$ cm$^{-1}$, respectively, we calculated:
a) for AFA algae, concentrations of 0.49 mg g$^{-1}$ DW for shinorine and 7.09 mg g$^{-1}$ DW for *porphyra*-334; the total MAAs content being thus equal to 0.76% algal DW;
b) For the Basic Extract, concentrations of 17-21 mg of MAAs (that is 1.7-2.1% DW).

These are significant data, as the whole AFA contains high constitutive levels of MAAs (0.76% DW), close to the maximal concentration found under UV exposure, i.e. 0.84%. (31) Also, we found that the extract has a higher concentration than the whole algae, reaching levels that are much higher than the maximal potential concentration.

MAAs (shinorine and *porphyra*-334) are structurally simple molecules, with a molecular weight of 300. This allows these water soluble molecules to easily cross the blood-brain barrier, confirming their ability to express their MAO-B inhibitory potential in the area where it is mostly needed, the brain.

Phycocyanins

The phycocyanins are present in the extract at a concentration of 8-10% (for the quantification, see below). Phycocyanins are the blue pigments typical of all cyanobacteria or blue-green algae, although with peculiar characteristics for each specific microalga. (32) As to functional and therapeutic properties of phycocyanins, research has mostly focused so far on those of the microalga *Spirulina*. The purified phycocyanins from *Spirulina* have shown to possess antioxidant (33) and anti-inflammatory (34, 35, 36) properties on different physiological systems such as liver (37), respiratory system (38) and brain (39, 40). Such properties of the purified PC from *Spirulina* can in general be attributed also to the phycocyanins of other algae, given their substantial similarity. Nevertheless, there can exist species-specific differences in the different phycocyanins from different microalgae which can lead to a different potency in the explication of the above described functional and therapeutic properties.

Structural Determination and Specific Characteristics of the Klamath Algae's Phycobilisomes.

Generally speaking, in the intact cyanobacterial cell phycocyanins (PC) are present inside the phycobilisome in the functional form $(\alpha\beta)_6$ (41). Following the break-up of the cell, the protein can be found in different aggregation states (monomers, dimers, trimers, hexamers) according to the organism analyzed. In the case of Klamath algae, the electrophoretic analysis of the PC, both as contained in the extract and as purified from the extract itself, has shown that the protein is found for the most part in its trimeric form $(\alpha\beta)_3$, with a total molecular weight of 121000. A monomer $\alpha\beta$ weighs approximately 40000 (18500 subunit $\alpha$+21900 subunit $\beta$). The majority of the studies on the purified FC from *Spirulina* tell us instead that the protein is found in *Spirulina* in the monomeric form $\alpha\beta$ with a molecular weight of approximately 37500, thus showing a different aggregation state relative to the purified PC from AFA.

The chromatographic analysis of the AFA's phycobilosomes has also shown that, as in other cyanobacterial species, the $\alpha$ subunit of PC binds a prosthetic group, while the $\beta$ subunit binds two. The prosthetic group or chromophore is called phycocyanobilin (PCB) and is responsible both of the blue color of the protein and of its antioxidant power (42).

A fundamental difference between AFA and *Spirulina* rests on the different structure of the phycobilisome. As opposed to *Spirulina*, the phycobilisome of AFA Klamath does not contain the pigment allo-phycocyanin, but only the pigment c-phycocyanin bound to a structural component which is missing in *Spirulina*, namely phycoerythrocyanin (PEC). FEC is a photosynthetic pigment which as of today has been identified only in a limited number of cyanobacterial species (43). PEC has a chemical structure very similar to that of FC, being composed by the two subunits $\alpha$ e $\beta$ which associate to form monomers and trimers. Nevertheless, while every monomer of PC binds 3 molecules of PCB, PEC possesses the unique characteristic of binding two molecules of PCB to the subunit $\beta$ and one molecule of phycoviolobilin (PVB) to the $\alpha$ subunit, which is responsible of the purple color of the pigment.

This absolutely is the first time that the phycobilisome of Klamath algae is defined as peculiarly constituted by the union of C-phycocyanin and phycoerythrocyanin, and this different qualitative structure of the phycobilisome of AFA Klamath algae adds a further decisive factor distinguishing AFA from *Spirulina*.

Figure 4:
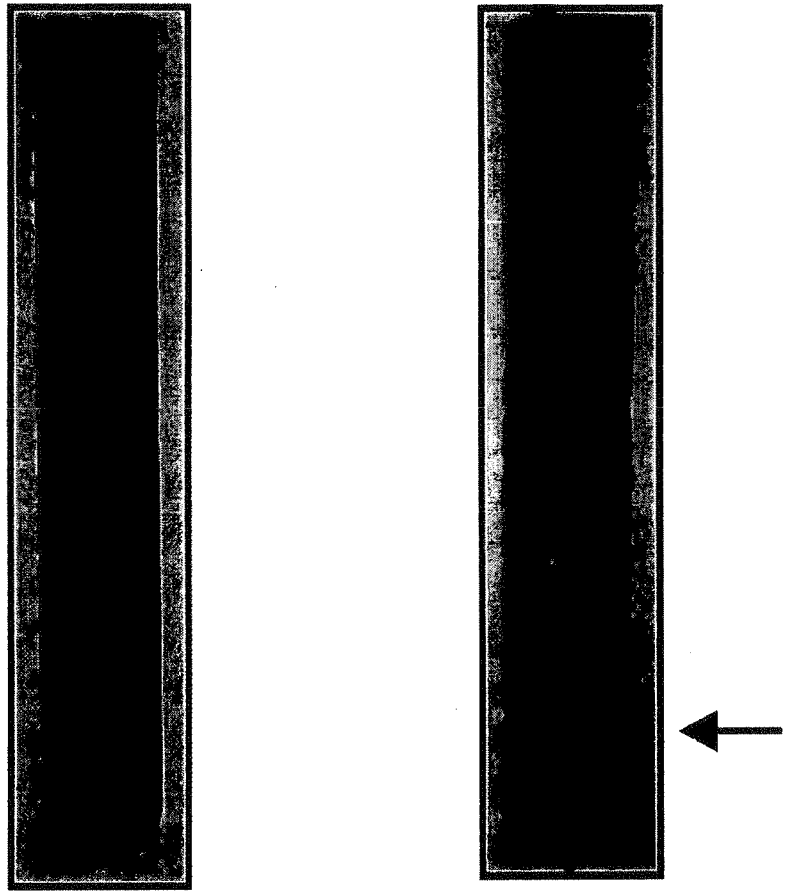
FIG. 4 shows a comparison of components of a cellular lysate of AFA with those of a Synechocystis PCC 6803 cyanobacterium.

FIG. 4 confirms what has been said, comparing the components of the cellular lysate of AFA with those of another well known cyanobacterium, *Synechocystis* PCC 6803. In both cyanobacteria it possible to see the blue band representing the phycobilisome, but in AFA algae the phycobilisome presents a lower molecular mass, confirming that, as opposed to common microalgae such as *Spirulina*, in the AFA phycobilisome only phycocyanins, but not allo-phycocianins, are present. Furthermore, the Figure shows that in AFA is also present a light purple band (shown by the arrow) which is typical of phycocerythrocyanins, thus proving their presence in the phycobilisome of Klamath algae.

To deepen the definition, each blue band has been further analyzed through HPLC connected to mass spectrometer (RP-HPLC-ESI-MS). Thanks to the different times of retention, the proteins of the phycobilisome have been separated and identified based on their molecular mass. The results obtained are shown in the following tables. First we see that while in *Synechocystis* (Table 1) both phycocyanin (cpcA at 28.2 min and cpcB at 28.9 min) and allo-phycocyanin (apcA at 30.7 min and apcB at 31.2 min), in AFA (Table 2) only phycocyanin (cpcA at 28.8 min and cpcB at 30.0 min) is present. Secondly, in AFA a protein with molecular mass of 19469 has been identified which is not present in *Synechocystis* and which corresponds to the beta subunit of the phycoerythrocyanin with two bilins attached (pecB a 25.0 min).

TABLE 1 proteins present in the phycobilisome of *Synechocystis*.

| Retention time (min) | Measured molecular mass | Expected molecular mass | Protein [homologous organism] | NCBI Number of access |
|---|---|---|---|---|
| 14.5 | 9322 | 9322 | cpcD | gi\|16329820 |
| 22.6 | 32505 | 32520 | CpcC | gi\|16329821 |
|  | 32388 | 30797 | cpcC | gi\|16329822 |
| 24.6 | 28770 | 27392 | cpcG | gi\|16329710 |
| 24.8 | 28885 | 28522 | cpcG | gi\|16332194 |
| 28.2 | 18173 | 17586 | cpcA (sub $\alpha$ phycocyanin) | gi\|2493297 |
| 28.9 | 19313 | 18126 | cpcB (sub $\beta$ phycocyanin) | gi\|2493300 |
| 30.7 | 17866 | 17280 | apcA (sub $\alpha$ allophycocyanin) | gi\|266765 |
| 31.2 | 17816 | 17215 | apcB (sub $\beta$ allophycocyanin) | gi\|266766 |

TABLE 2 proteins present in the phycobilisome of AFA Klamath algae

| Retention time (min) | Measured molecular mass | Expected molecular mass | Protein [homologous organism] | NCBI Number of access |
|---|---|---|---|---|
| 15.2 | 9031 | 8925 | hypothetical protein Avar03000795 [*Anabaena variabilis* ATCC 29413] | gi\|45510540 |
|  |  | 8895 | cpcD [*Nostoc* sp. PCC 7120] | gi\|131740 |
| 25.0 | 19469 | 18284 | pecB: | gi\|548504 |

TABLE 2-continued proteins present in the phycobilisome of AFA Klamath algae

| Retention time (min) | Measured molecular mass | Expected molecular mass | Protein [homologous organism] | NCBI Number of access |
|---|---|---|---|---|
| | 19308 | | phycoerythrocyanin beta chain [*Nostoc* sp. PCC 7120] | |
| | | 18370 | hypothetical protein Avar03000787 (pecB) [*Anabaena variabilis* ATCC 29413] | gi|45510532 |
| 26.4 | 31044 | 32078 | cpcC [*Nostoc* sp. PCC 7120] | gi|20141679 |
| | | 32219 | hypothetical protein Avar03000794 (rod linker Mw 32000) [*Anabaena variabilis* ATCC 29413] | gi|45510539 |
| | | 31295 | pecC [*Nostoc* sp. PCC 7120] | gi|464511 |
| | | 31304 | hypothetical protein Avar03000789 (pecC) [*Anabaena variabilis* ATCC 29413] | gi|45510534 |
| | 30124 | 29333 | hypothetical protein Avar03000801 (cpcG4) [*Anabaena variabilis* ATCC 29413] | gi|46135436 |
| 26.8 | 26119 | 28637 | hypothetical protein Avar03000799 (cpcG2) [*Anabaena variabilis* ATCC 29413] | gi|45510544 |
| 27.8 | 10994 | 10986 | fdxH2: ferredoxin vegetative [*Anabaena variabilis*] | gi|1169673 |
| 28.8 | 17714 | 17457 | cpcA [*Nostoc* sp. PCC 7120] | gi|9957319 |
| 30.0 | 19222 | 18332 | cpcB [*Nostoc* sp. PCC 7120] | gi|38894 |

Figure 5:
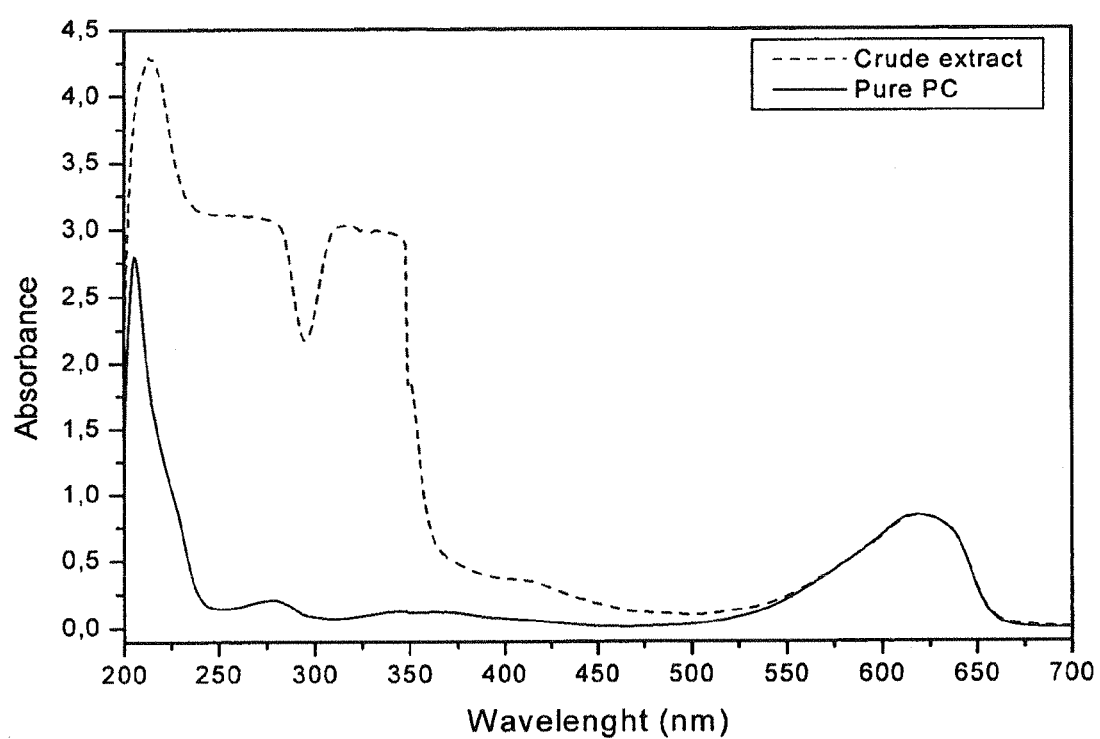
FIG. 5 shows the absorption of a crude extract of AFA and a purified sample of AFA-PC.

This unique structure is an important element to explain the stronger antioxidant and antinflammatory action of the whole AFA-PC relative to its PCB. Antioxidant and antinflammatory properties become relevant in this context insofar as they generate a strong neuroprotection; the whole PC is more powerful than its PCB also in terms of neuroprotection, which clearly indicates that the other active component besides PCB in the phycobilisome, namely PEC with its specific PVB chromophore, is very likely the most active health-enhancing principle in AFA-PC. That the purified AFA-PC does indeed contain not only the C-PC with its PCB chromophore, but also PEC and its PVB chromophore is evident by looking at the spectrometry of the extract resulting from the purification (FIG. 5). In fact, the absorption maximum of C-PC is 620 nm, which in the spectrometry of FIG. 5 represents the top of the peak. But the absorption maximum of PEC is known to be 566 nm for the α-subunit (phycoviolobilin or PVB) and respectively 593 nm and 639 nm for the two PCBs of the β-subunit. All three values are indeed included in the bell-shaped peak constituting the spectrometric profile of the purified PC. In consideration of the strong link, very difficult to break, between C-PC and PEC in AFA algae, this confirms that besides the C-PC, also the PEC is necessarily part of the purified PC extract. This in turn means that the PC from AFA is significantly different, both structurally and functionally, from the PCs of other cyanobacteria, including the one from *Spirulina*, on which most studies have been done; and that this difference consists in having only one part in common, namely C-PC, but not the other; with the consequence that, while the properties of C-PC can also be attributed to the C-PC component of the AFA-PC, the properties of the whole PC from AFA, in its being a C-PC/PEC complex (including its chromophores PCB and PVB), are exclusively attributable to it (as well as to any C-PC/PEC complex present in any other microalgae).

Purification Methodologies (FIG. 5)

PC was purified from the dried AFA extract as follows:
suspend 500 mg of extract in 50 ml of 100 mM Na-phosphate buffer pH 7.4;
centrifuge at 2500 rpm for 10' at 4° C.;
gather the supernatant and add solid ammonium sulfate to a 50% saturation;
precipitate the proteins for 60 min at 4° C. while keeping the sample in agitation;
centrifuge at 10,000 rpm for 30 min at 4° C.;
discard the clear colourless supernatant and resuspend the blue precipitate in a small volume of 5 mM Na-phosphate buffer pH 7.4;
dialyse overnight at 4° C. against the same buffer;
place the dialysed PC in a hydroxyapatite column balanced with 5 mM Na-phosphate buffer pH 7.4;
elute the sample with Na-phosphate buffer pH 7.0 of increasing ionic strength (from 5 to 150 mM);
gather the fractions and read the absorbance at 620 nm and 280 nm with the spectrophotometer;
pool the fractions in which $Abs_{620}/Abs_{280}>4$ (index of pure PC);
precipitate the PC with ammonium sulfate at 50% saturation for 1 hour at 4°;

centrifuge at 10,000 rpm for 30' at 4° C.;
discard the supernatant and suspend again the PC in a 150 mM of Na-phosphate buffer Ph 7.4;
dialyse against the same buffer at 4° C.;
transfer the purified PC in a flask and store in darkness at +4° C. or 20° C.

Quantification of Phycocianin

To measure the molar concentration of pure PC we used its coefficient of molar estinction ε at 620 nm, which for the trimeric form $(\alpha\beta)_3$ is equal to 770000 $M^{-1}$ $cm^{-1}$. This means that a solution of 1 M of PC at 620 nm has an absorption value of 770000.

To measure the concentration of PC in the extract we use the coefficient of specific extinction $E^{1\%}$ at 620 nm of 70 $g^{-1}$ $cm^{-1}$. This means that a solution containing 1% of PC (that is 1 g/100 ml) at 620 nm absorbs 70. Based on these calculations, the average content of PC in the extract is equal to 80-100 mg/g DW (8-10% DW).

Figure 6:
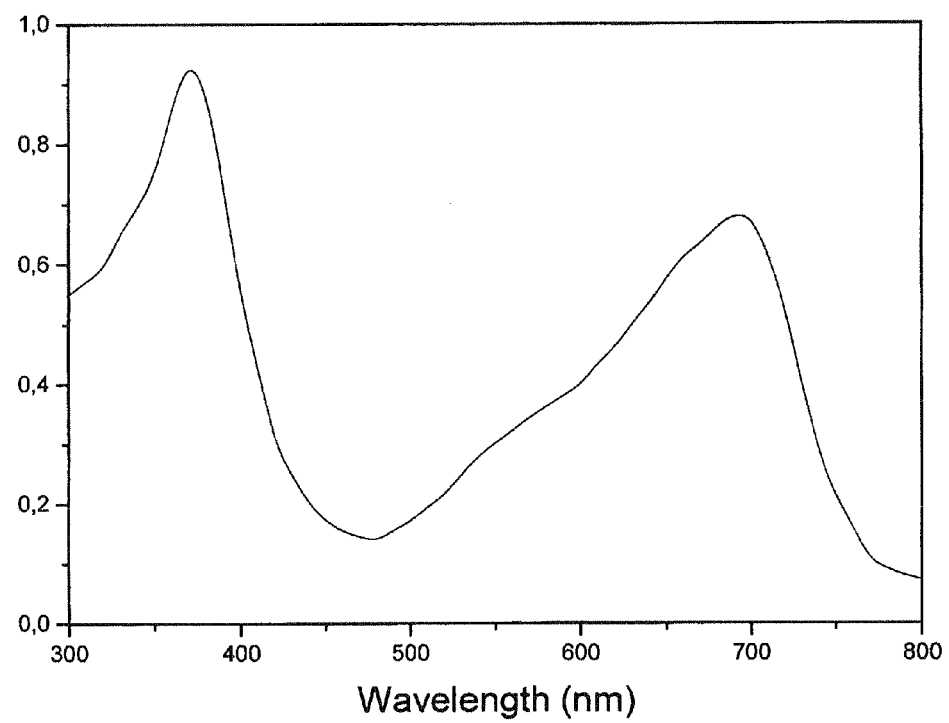
FIG. 6 shows the absorption of a purified AFA-PCB chromophore.

Purification of the PCB Chromophore (FIG. 6)

Suspend 500 mg of extract in 50 ml of distilled $H_2O$.
Centrifuge at 2500 rpm for 10' at 4° C.
Decant the deep blue supernatant and precipitate the PC with trichloroacetic acid at 1%.
Incubate for 1 h in the dark at 4° C., while agitating.
Centrifuge at 10000 rpm for 30' at 4° C.
Gather the pellet containing PC and wash 3 times with methanol.
Re-suspend the pellet in 10 ml of methanol containing 1 mg/ml of $HgCl_2$.
Incubate for 20 h at 42° C. in darkness to release the PCB from PC.
Centrifuge at 2500 rpm for 10' to remove the proteins.
Add to the supernatant containing PCB β-mercaptoethanol (1 μl/ml) to precipitate the $HgCl_2$.
Incubate at −20° C. for 24 h.
Centrifuge at 10000 rpm for 30' at 4° C. to remove the white precipitate.
Add to the supernatant 10 ml of methylene chloride/butanol (2:1, v/v).
Wash with 20 ml of distilled $H_2O$ and centrifuge at 3000 rpm for 10'.
Remove the upper phase, harvest the lower part containing PCB.
Wash the PCB in 15 ml $H_2O$ 3 times.
Dry under nitrogen and store at −20° C.

Evaluation of the MAO-B Inhibition by AFA Klamath Extract and by its Constitutive Active Principles Phytochrome, Phycocyanin and MAAs We have tested the MAO-B inhibitory activity of the Basic Extract using the specific substrate benzylamine (1 mM). The test was performed by a spectrophotometer at 30° C. with a wavelength of 250 nm, by pre-incubating MAO-B (2 μg/ml) with different concentrations of the water-soluble and lipid-soluble components of the basic extract, as produced by the steps a) to c) described above (initial concentration 10 mg/ml). The water-soluble component-enriched extract has been prepared by re-suspending the aqueous extract in water and collecting the supernatant after centrifugation. The lipophilic component-enriched soluble extract has been obtained by re-suspending the extract in acetone; afterwards the supernatant has been dried, and the pellet has been re-suspended in DMSO, a solvent compatible with the dosage of MAO-B.

Figure 7A:
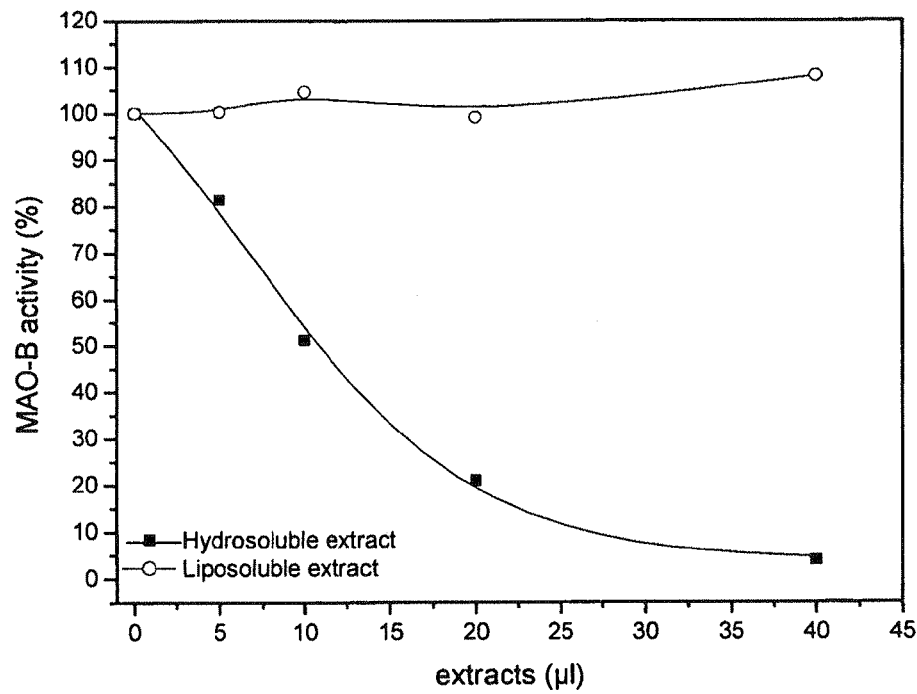
FIG. 7A compares the MAO-B activity of a water-soluble fraction and a lipophilic fraction of an AFA extract.
Figure 7B:
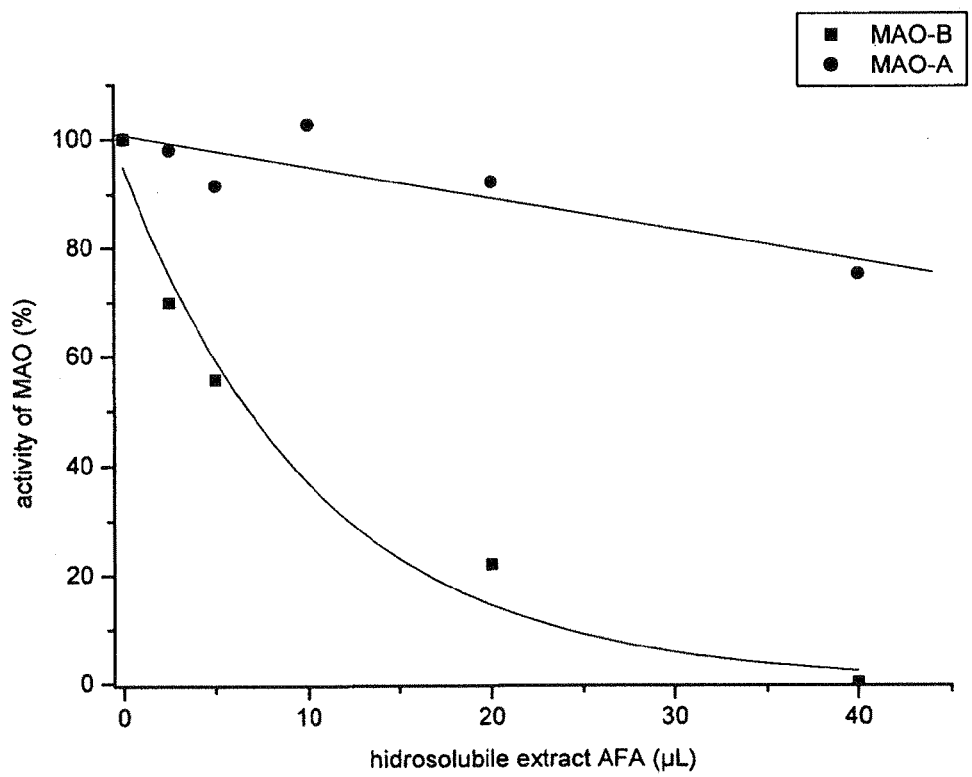
FIG. 7B compares the MAO-A and MAO-B activity of a water-soluble fraction of an AFA extract.

As shown in FIG. 7A, the water-soluble fraction inhibits MAO-B in a dose-dependent manner, while the lipophilic fraction does not inhibit the enzyme. The water-soluble fraction of the AFA Basic Extract is a potent selective MAO-B inhibitor, with an $IC_{50}$ of 6.9 μL. Its MAO-B selectivity is 4 ($IC_{50}$ MAO-B/$IC_{50}$ MAO-A>4.05) (FIG. 7B).

Figure 8:
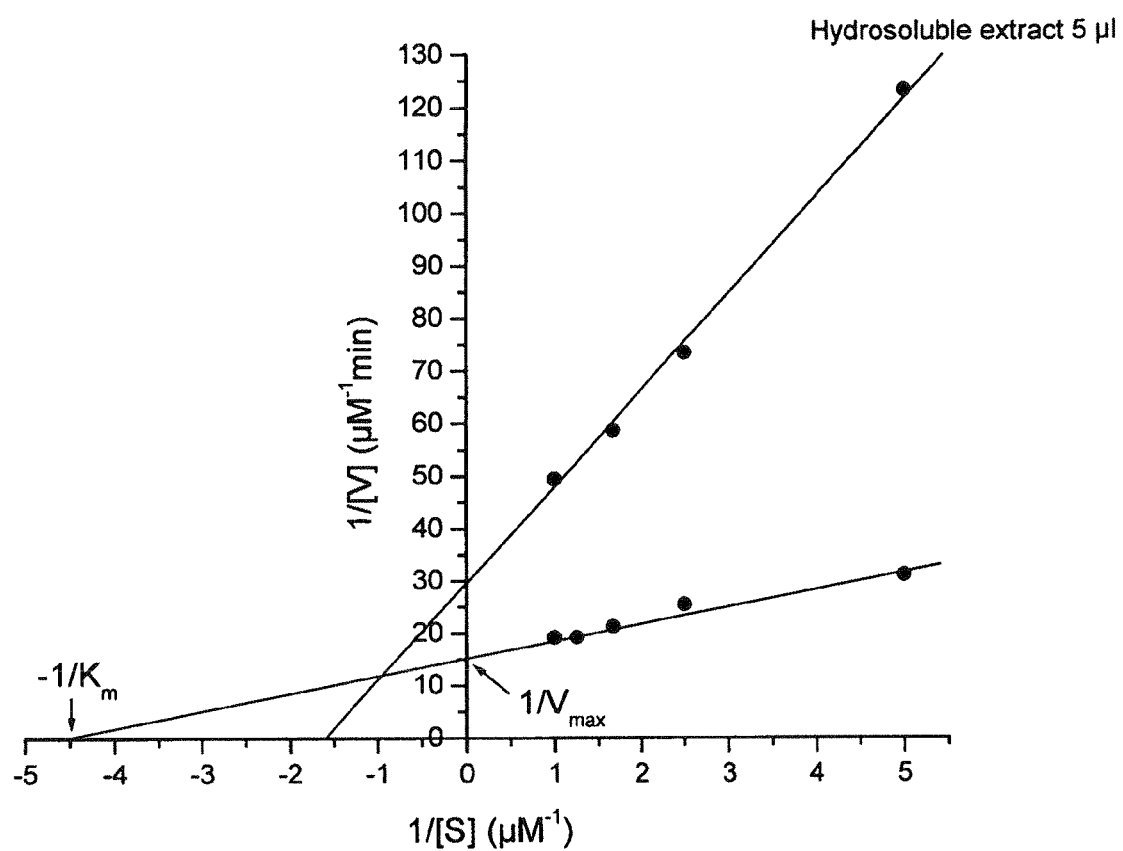
FIG. 8 shows a Lineweaver-Burk plot of a water-soluble fraction of an AFA extract.

The Lineweaver-Burk plot in FIG. 8 shows that such inhibition is reversible and of a mixed type in relation to competition, with a decrease in the $V_{max}$ and increase of the Michaelis-Menten $K_m$ constant. Plotting the slope vs. the concentration of the hydrosoluble fraction of the AFA extract, a 1 μL inhibition constant $K_i$, is obtained. Compared to the hydrosoluble fraction of the Basic Extract, this low $K_i$ value indicates a high affinity for the MAO-B enzyme.

The fact that the extract's inhibition is reversible means that it performs a physiological activity plausibly devoid of side effects. As to the mixed competition, it is very likely due to the complex nature of the extract, including different functional molecules, some competitive and others non-competitive. The main active components of the extract are the AFA-phytochrome (0.5% DW); phycocyanins (8-10% DW); and the MAAs or mycosporine-like aminoacids (1.7-2.1% DW), which we have tested individually as MAO-B inhibitors.

MAO-B Inhibition by Phycocyanins

Figure 9:
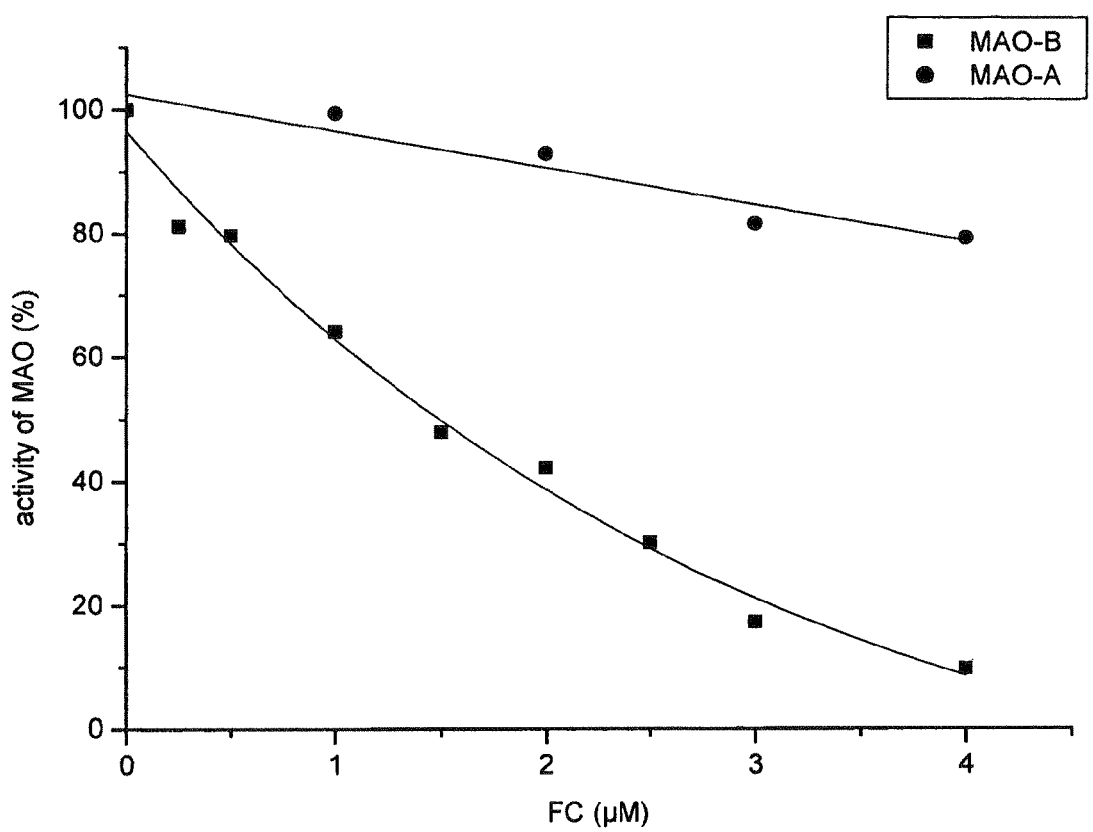
FIG. 9 shows the MAO-B activity of a purified AFA-PC sample.

The test has been done through a spectrophotometer at 30° C. with a wavelength of 250 nm, using benzylamine as a substrate, by preincubating MAO-B with various concentrations of purified PC from AFA (0.5-4 μM). As shown in FIG. 9, AFA-PC causes a dose-dependent decrease of MAO-B activity, with an $IC_{50}$ of 1.44 μM. The MAO-B selectivity of AFA-PC is higher than 3.5 (IC50MAO-B/IC50MAO-A>3.5).

Figure 10:
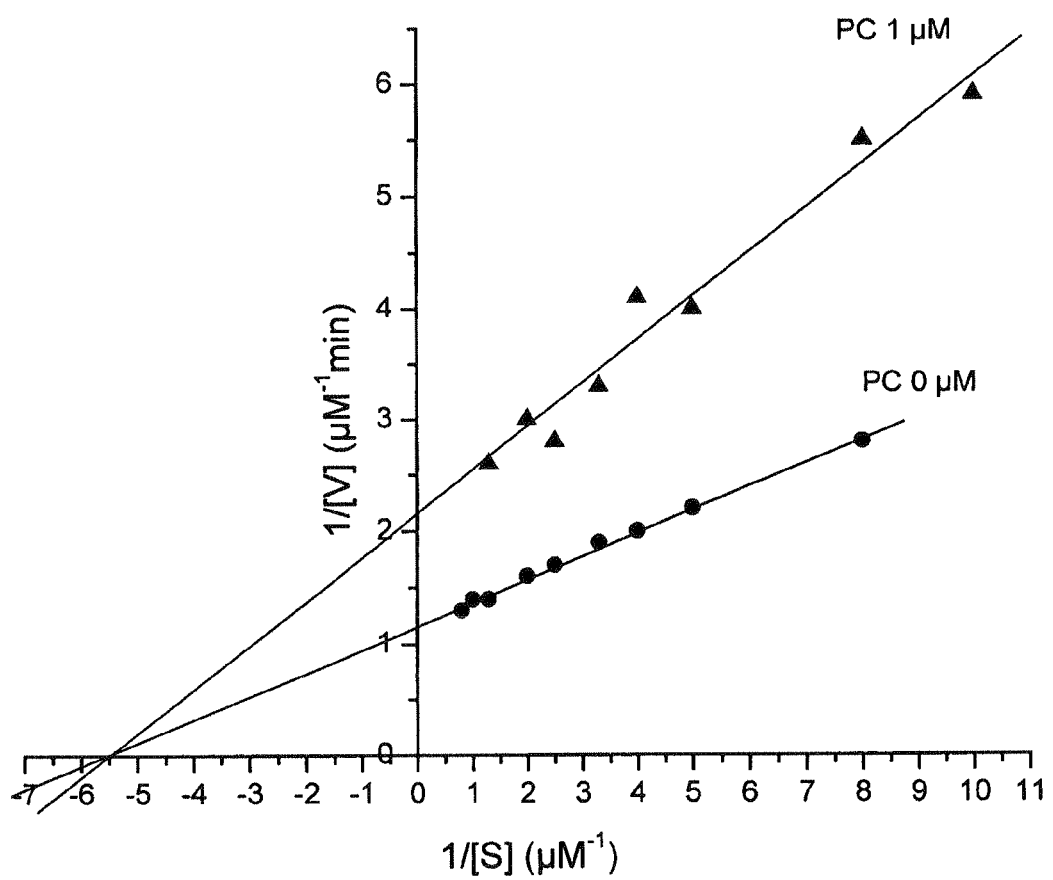
FIG. 10 shows a Lineweaver-Burk plot of a purified AFA-PC sample.

The Lineweaver-Burk plot in FIG. 10 shows that, as with the extract, the inhibition is reversible and of a mixed type (competitive and non-competitive) with modification of both Vmax and Km.

By plotting the slope vs. the PC concentration we obtain the value of the inhibition constant $K_i$, which here is of 1.06 μM. The inhibition constant measures the affinity of the inhibitor for the enzyme: a high $K_i$ indicates a low affinity for the enzyme and viceversa. In this instance, the low $K_i$ value indicates a high affinity of AFA PC towards MAO-B.

MAO-B Inhibition by MAAs

Figure 11:
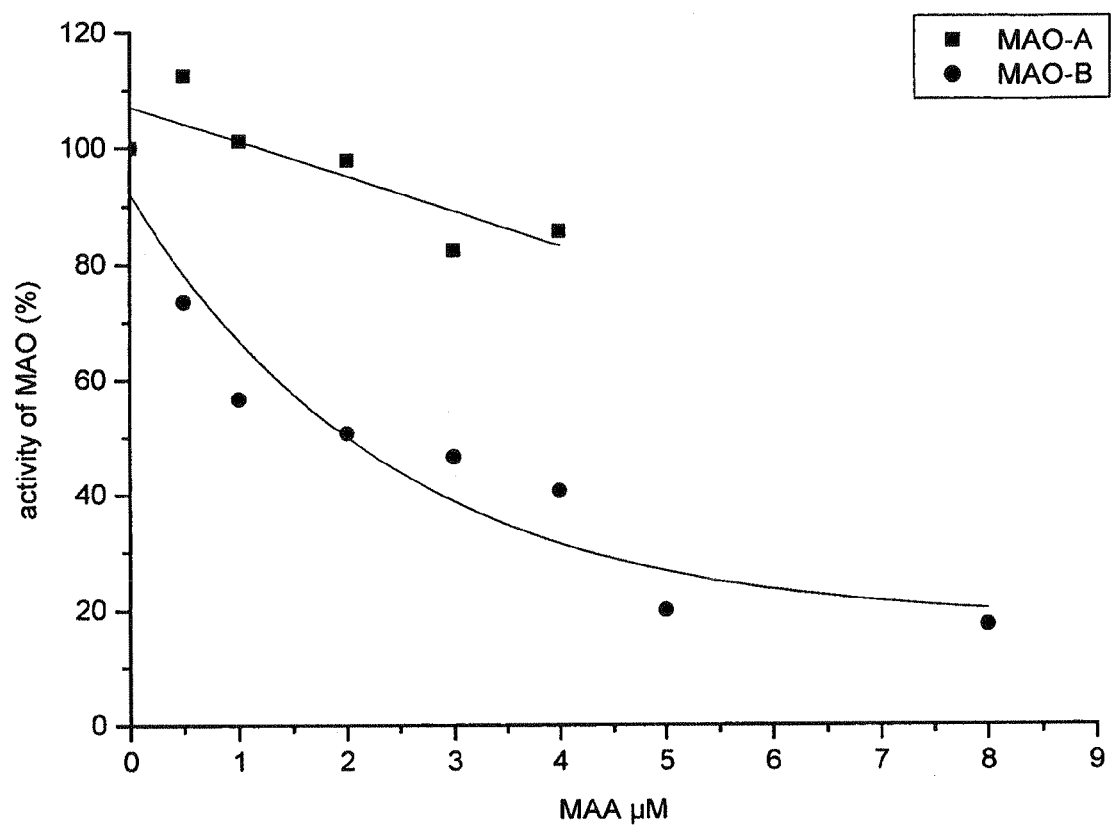
FIG. 11 shows the MAO-A and MAO-B activity of MAAs from an AFA sample.

The activity of MAO-B on a benzylamine substrate has been evaluated in relation to increasing concentrations of MAAs (0.5-8 μM), previously purified from the Basic Extract with 20% methanol. FIG. 11 shows the dose-dependent MAO-B inhibition by MAAs, with an $IC_{50}$ of 1.98 μM. The MAO-B selectivity of MAAs is higher than 2 ($IC_{50}$MAO-B/$IC_{50}$MAO-A>2.02).

Figure 12:
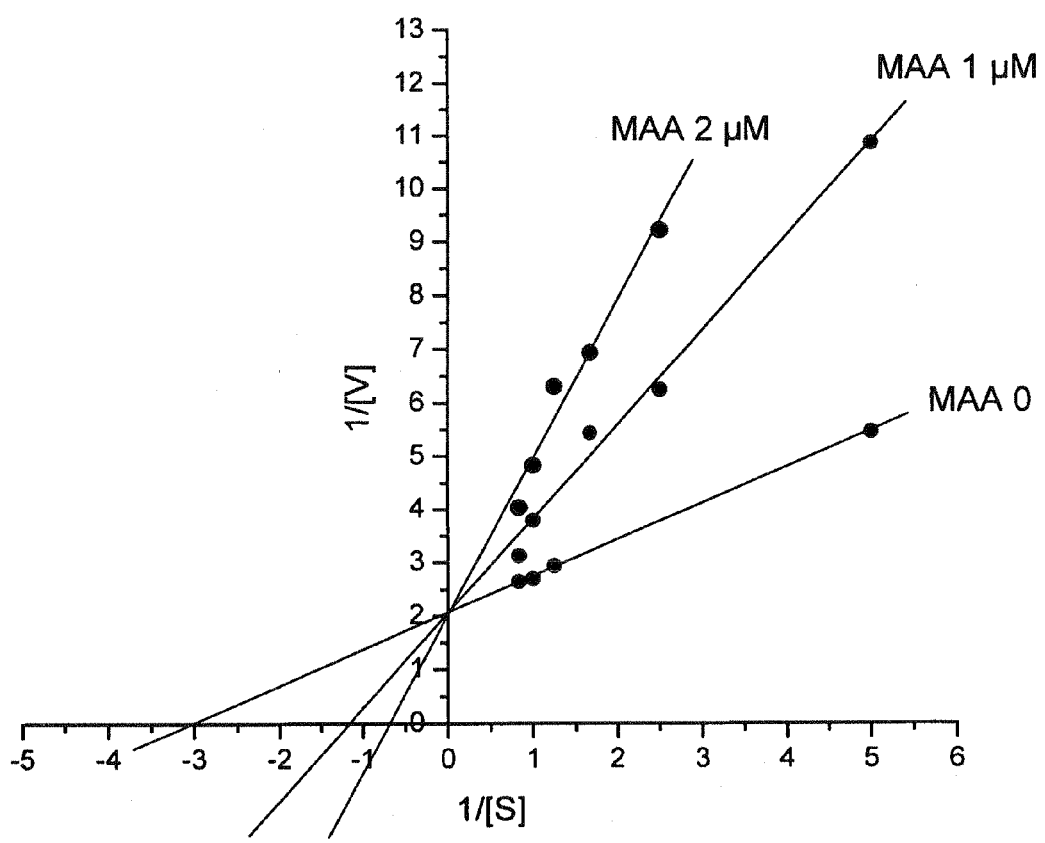
FIG. 12 shows a Lineweaver-Burk plot of MAAs from an AFA sample.
Figure 13:
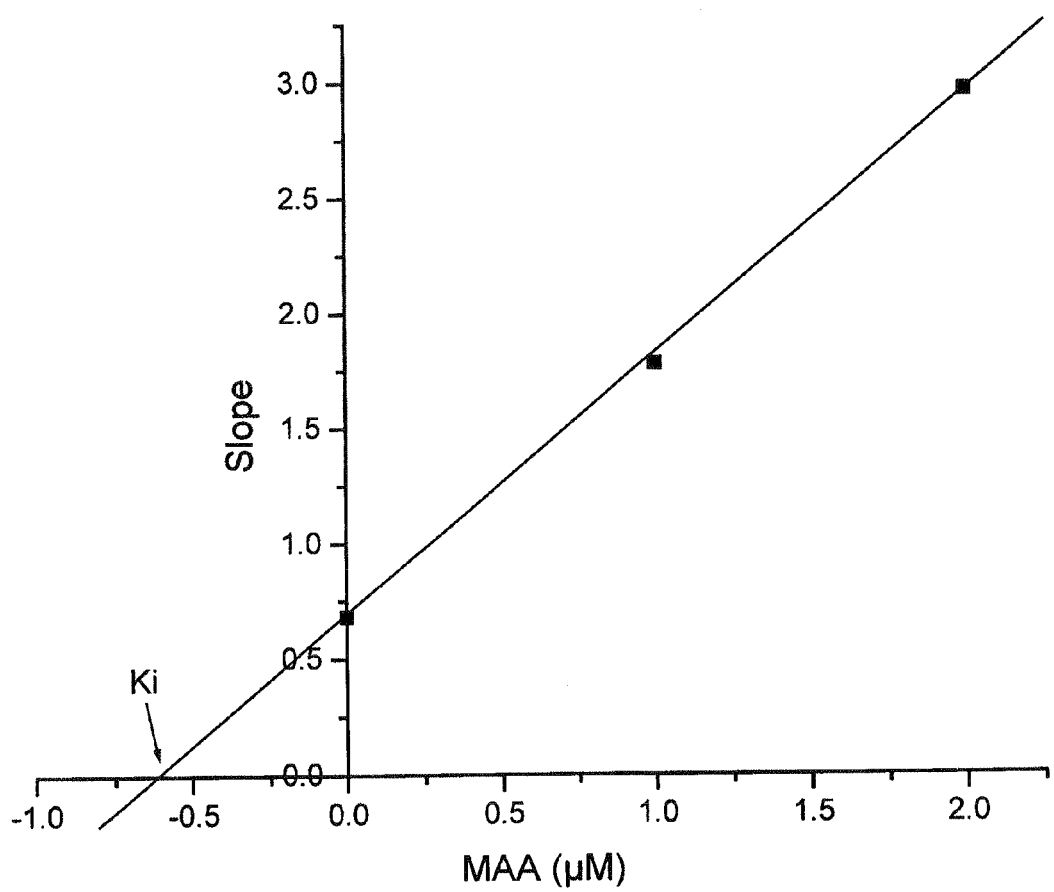
FIG. 13 shows a graph of slope versus concentration of MAAs from an AFA sample.

The Lineweaver-Burk plot (FIG. 12) shows that the inhibition is both reversible and competitive, with an increase of $K_m$ but no variation of the $V_{max}$. This means that MAAs, thanks to their chemical structure, compete with the substrate for the link to the active site of the enzyme. Plotting the slope vs. the concentration of MAAs (FIG. 13) we obtain the value of the inhibition constant $K_i$, which is of 0.585 μM, which demonstrates a very high degree of affinity for the enzyme.

MAO-B Inhibition by AFA Phytochrome

Figure 15:
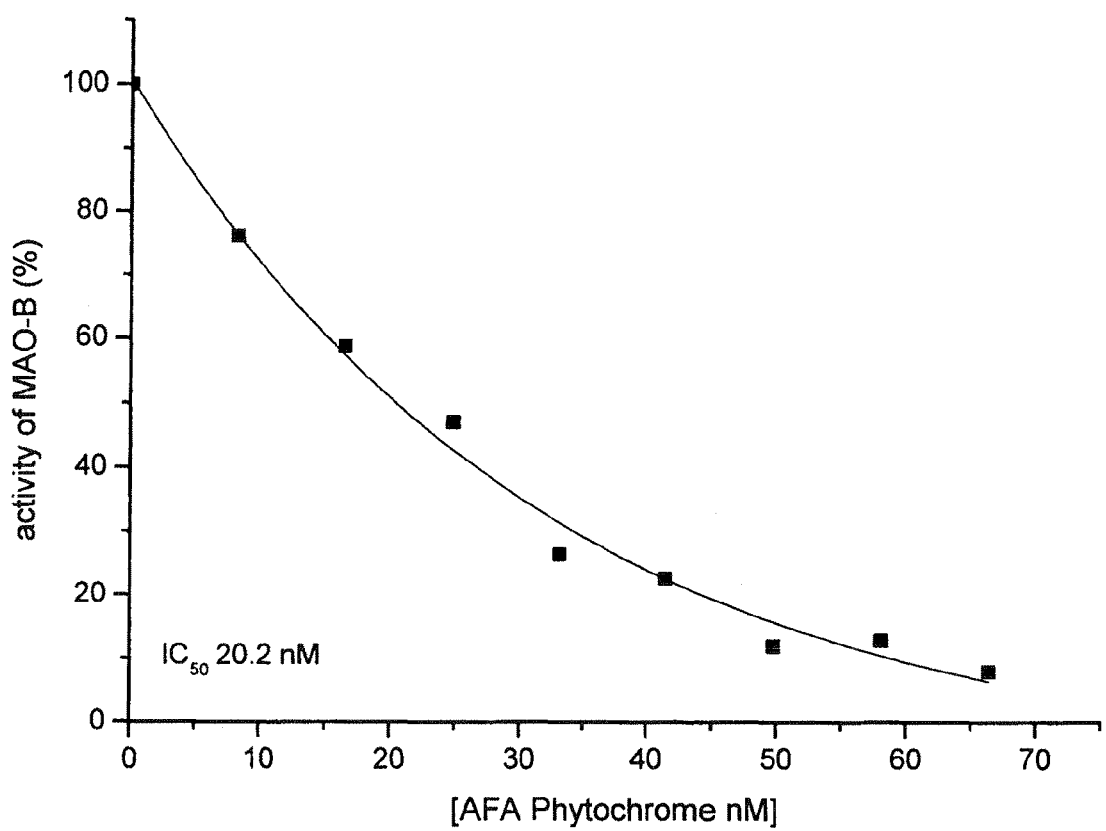
FIG. 15 shows the dose-dependent MAO-B activity of an AFA phytochrome.

The test has been done through a spectrophotometer at 30° C. with a wavelength of 250 nm, using benzylamine as a substrate, by preincubating MAO-B with various concentrations of purified AFA phytochrome (8.3-66.4 nM). As shown in FIG. 15, AFA phytochrome causes a dose-dependent decrease of MAO-B activity, with an $IC_{50}$ as low as 20.2 nM.

Figure 16:
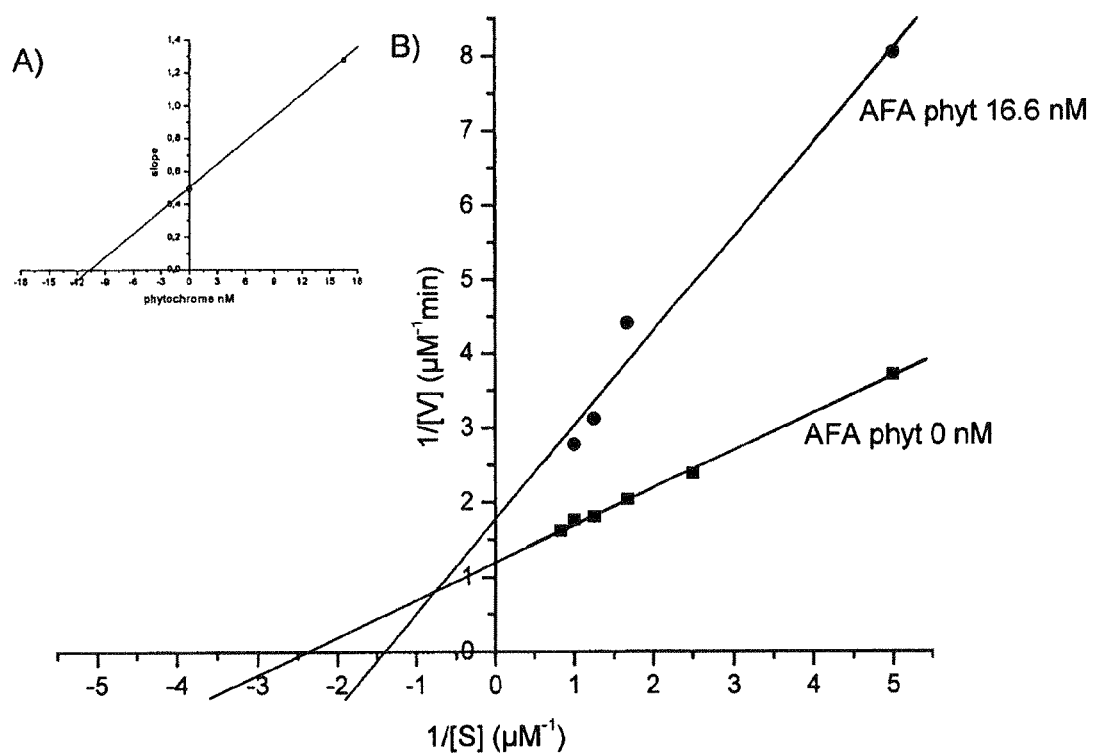
FIG. 16 shows a Lineweaver-Burk plot of an AFA phytochrome.

The Lineweaver-Burk plot in FIG. 16 shows that, as with the extract, the inhibition is reversible of a mixed type (competitive and non-competitive) with modification of both $V_{max}$ and $K_m$.

By plotting the slope vs. the AFA phytochrome concentration we obtain the value of the inhibition constant $K_i$, which here is of 10.48 nM. The inhibition constant measures the affinity of the inhibitor for the enzyme: a high $K_i$ indicates a low affinity for the enzyme and viceversa. In this instance, the extremely low $K_i$ value indicates a very high affinity of AFA phytochrome towards MAO-B.

The competitive and reversible action of the MAAs makes these molecules very potent in the inhibition of MAO-B. Indeed, the competitive and reversible character of the MAO-B inhibition assures at the same time high efficacy and a physiological and side-effects free activity. In this sense, the MAAs contained in the extract, also due to their molecular weight and consequent ability to easily cross the blood-brain barrier, constitute a decisive component, even in vivo, in order to generate the therapeutic effects derived from MAO-B inhibition.

Even more than MAAs, the phytochrome has proven to be the most powerful MAO B inhibitor of all known substances to date. Its very high affinity for the MAO-B enzyme, and its effective inhibition at dosages of few nanomolars, make this molecule not only a perfect therapeutic agent on its own, but the factor that seems to provide the most important contribution to the high neurological effectiveness of the AFA extract(s).

It should be added that some of the considerations relating to the MAAs and phythcrome can also be applied to the in vivo behaviour of phycocyanins. We know that PC generate neuroprotective effects on the brain in vivo, and so that they are able to cross the blood-brain barrier. (44) This means that they are also able to realize in vivo their MAO-B inhibitory activity in the brain. The molecular weight of the chromophore is indeed only 700, that is not much more than the molecular weight of the MAAs. The same holds true for the chromophore of the phytochrome, the phytochromobilin, structurally similar to phycocyanobilin.

In conclusion, the activity of MAO-B inhibition on the part of the extract and its active components, AFA phytochrome, AFA-PC and MAAs, is extremely relevant, as both the molecules and the extract place themselves at the highest level of activity, equal or higher than the pharmacological substances, and greatly superior to any natural molecule tested, as shown in the following table (45):

TABLE 3

Comparative kinetics parameters ($IC_{50}$ e $K_i$) of MAO B inhibition from known synthetic and natural inhibitors.

| MAO-B Inhibitors | $IC_{50}$ | $K_i$ | Inhibition type |
|---|---|---|---|
| Deprenyl | 0.31 µM | 0.002 µM | Irreversible |
| Epicatechine | 58.9 µM | 21 µM | Mixed |
| Catechine | 88.6 µM | 74 µM | Mixed |
| Non Harman alkaloid | 6.47 µM | 1.12 µM | Mixed |
| Piperine | 91.3 µM | 79.9 µM | Competitive |
| Paeonol | 42.5 µM | 38.2 µM | Competitive |
| Emodin | 35.4 µM | 15.1 µM | Mixed |
| AFA phycocyanin | 1.44 µM | 1.06 µM | Mixed |
| AFA MAAs | 1.98 µM | 0.585 µM | Competitive |
| AFA phytochrome | 0.02 µM | 0.010 µM | Mixed |

As shown by the table, only phycocyanins and MAAs have an IC50 slightly higher than 1 µM, thus very close to that of Deprenyl (0.31 µM), and tens of times lower than the IC50 of the other molecules considered. AFA phytochrome, on the other hand, has an IC50 15 times lower than that of Deprenyl. The same is true for the inhibition constant $K_i$ which measures the affinity of the inhibitor for the enzyme. AFA-phycocyanins have a $K_i$ of around 1 µM, like the non Harman alkaloids of coffee and tobacco (but of course without any of the problems associated with those two substances). On the other hand, MAAs and the AFA phytochrome are the only molecules, together with Deprenyl, to have a $K_i$ lower than 1 µM, and so a very high affinity for the MAO-B. In fact, AFA phytochrome is the only natural molecule, besides selegyline/Deprenyl, whose $K_i$ is in the order of a few nanomolars. And yet, there is an essential difference between selegiline/Deprenyl and the molecules of the AFA extract: the former is an irreversible inhibitor, thus characterized by potential side effects; whereas AFA Klamath MAO B inhibiting molecules are all reversible, characterized by a physiological activity devoid of the problems associated with synthetic molecules.

Figure 14:
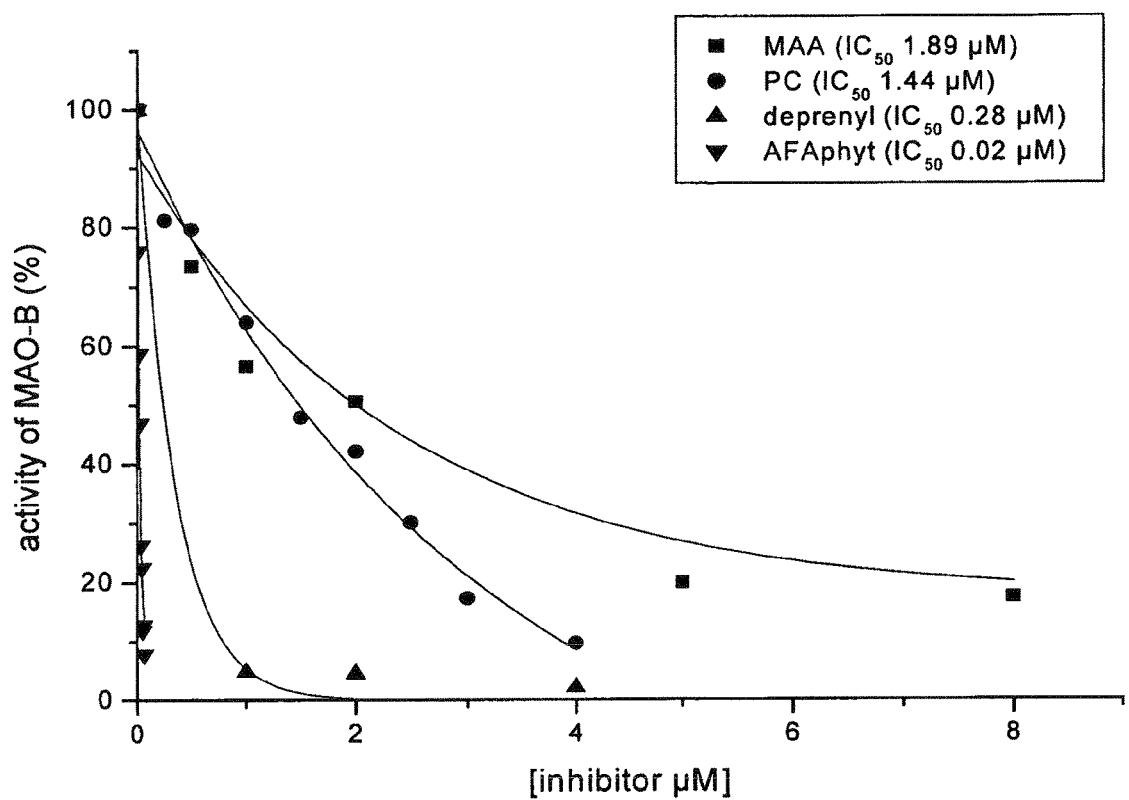
FIG. 14 shows the MAO-B inhibitory activity of the three molecules of AFA.
Figure 17:
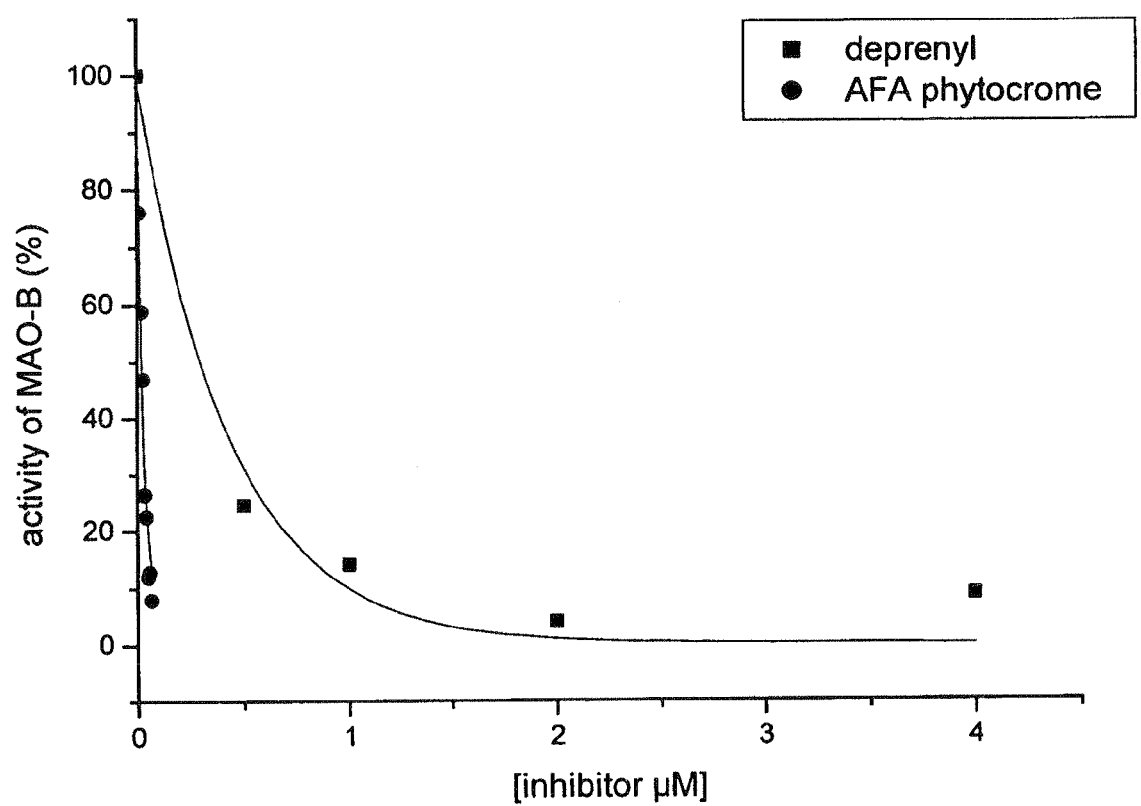
FIG. 17 shows the MAO-B activity of an AFA phytochrome.

FIG. 14 shows graphically the MAO-B inhibitory activity of the three molecules of AFA in relation to Deprenyl. Given the synergy of all three molecules in the Basic Extract (and other AFA extracts), the overall MAO-B inhibitory activity of the Basic Extract results very high. Something that becomes particularly relevant considering also the high quantity of PEA present in it. If we compare the basic extract with deprenyl on the base of its PC content, we obtain that the Basic Extract reaches the IC50 at a PC dosage as low as 0.05 µM, which would indicate a potency 7.5 times higher than Deprenyl (and tens of times higher than the natural substances). This makes sense in light of the potency of the phytochrome contained in the Basic Extract: in fact 7.5 times is an average between the inhibitory potency of PC and MAAs, which is slightly lower than Deprenyl, and that of the phytochrome, which is 15 times higher (FIG. 17). This also shows that the higher potency of the extract relative to the purified AFA-PC is for the most part due to the phytochrome.

Moreover, the extract still maintains the advantage of being a natural substance acting physiologically, whose MAO-B inhibition is reversible and mainly competitive, thus devoid of the side effects potentially associated with irreversible molecules such as Deprenyl and other synthetic substances. (46)

The further advantage of the extract is its high content of phenylethylamine, a powerful dopaminergic neuromodulator which works in total synergy with other molecules, a synergic activity that we can thus summarize:

Phenylethylamine or PEA has twofold dopaminergic activity, both as it stimulates the release of dopamine from the nigrostriatal tissue, and as it inhibits the post-synaptic reuptake of dopamine itself;

Phytochrome, MAAs and phycocyanins, as powerful MAO-B inhibitors, also increase dopaminergic transmission insofar as a reduced activity MAO-B implies a longer life of neuroamines, including dopamine;

Phytochrome, MAAs and phycocyanins, as MAO-B inhibitors, also prolong the life and activity of phenylethylamine, which is itself the object of the deamination activity of the MAO-B enzyme, with the consequent creation of a virtuous circle of further support to dopaminergic transmission and activity and to the more general neuromodulation produced by PEA.

Finally, the powerful antioxidant and anti-inflammatory activity of phycocyanins, together with their or their chromophore ability to cross the blood-brain barrier; as well as the extremely high antioxidant activity of the phytochrome and the less strong yet significant antioxidant activity of MAAs, generates a neuroprotection that shields the different active molecules and more generally the neurological virtuous cycle they create, from any oxidative and inflammatory damage.

Neuroprotection

We have tested the neuroprotectant properties of the AFA extract, the specific AFA-PC and its chromophore PCB, as well as MAA's against the neurotoxic effect of glutamate.

Glutamate is the main excitatory neurotransmitter in the mammalian central nervous system, but over-stimulation of its NMDA subtype receptor in neurons triggers a massive intracellular accumulation of $Ca^{2+}$, leading to cell death. In addition intramitochondrial $Ca^{2+}$ accumulation, after NMDA receptor stimulation, transient increases in free cytosolic $Ca^{2+}$ activate the neuronal isoform of nitric oxide synthase (NOS) (49), an enzyme that forms nitric oxide (NO.) or, mainly in primary neurons, its superoxide ($O2.^-$) reaction product, peroxynitrite ($ONOO^-$).

The exposure of neurons to glutamate was carried according to a slightly modified method (50): culture medium was removed and neurons were washed once with prewarmed 37° C. buffered Hanks' solution (5.26 mM KCl, 0.43 mM $KH_2H_2PO_4$, 132.4 mM NaCl, 4.09 mM $NaHCO_3$, 0.33 mM $Na_2HPO_4$, 20 mM glucose, 2 mM $CaCl_2$, and 20 mM HEPES, pH 7.4) and pre-incubated in the absence or presence of several concentrations of AFA extract (1-50 nM), PC (10-1000 nM), PCB (10-1000 nM) and MAA (1-10 µM) in prewarmed 37° C. buffered Hanks' solution. After 30 min of pre-incubation, L-glutamate was added from concentrated solutions to the final concentration indicated 100 µM plus 10 µM glycine. Neurons were incubated at 37° C. for 15 min, the buffer was aspirated, replaced with DMEM and the cells were incubated at 37° C. for further 24 h in the absence of effectors.

Apoptosis was assessed by staining the nuclei of cells with DAPI (50), a membrane-permeable fluorescent dye that binds DNA and allows quantification of apoptotic neurons, i.e., neurons displaying fragmented or condensed nuclei. Briefly, 24 h after glutamate exposure, neuronal cultures were washed with warm PBS (37° C.) and fixed with 4% (wt/vol) paraformaldehyde in PBS for 30 min at room temperature. After being washed with PBS, cells were exposed to 3 µM DAPI for 10 min at room temperature in the dark and were then washed twice with PBS. Cells were scored for chromatin condensation by fluorescence microscopy, using a fluorescein filter (330-380 excitation; 30× magnification). Total and apoptotic nuclei were counted. In all cases, approximately 600-1,000 cells were counted per well by an operator blind to the protocol design. Measurements from individual cultures were performed in duplicate and results are expressed as the mean S.E.M. values for the number of culture preparations indicated. Statistical analysis of the results was determined by Kruskal-Wallis test followed by the least significant difference multiple range test. In all cases, p–0.05 was considered significant.

Figure 18:
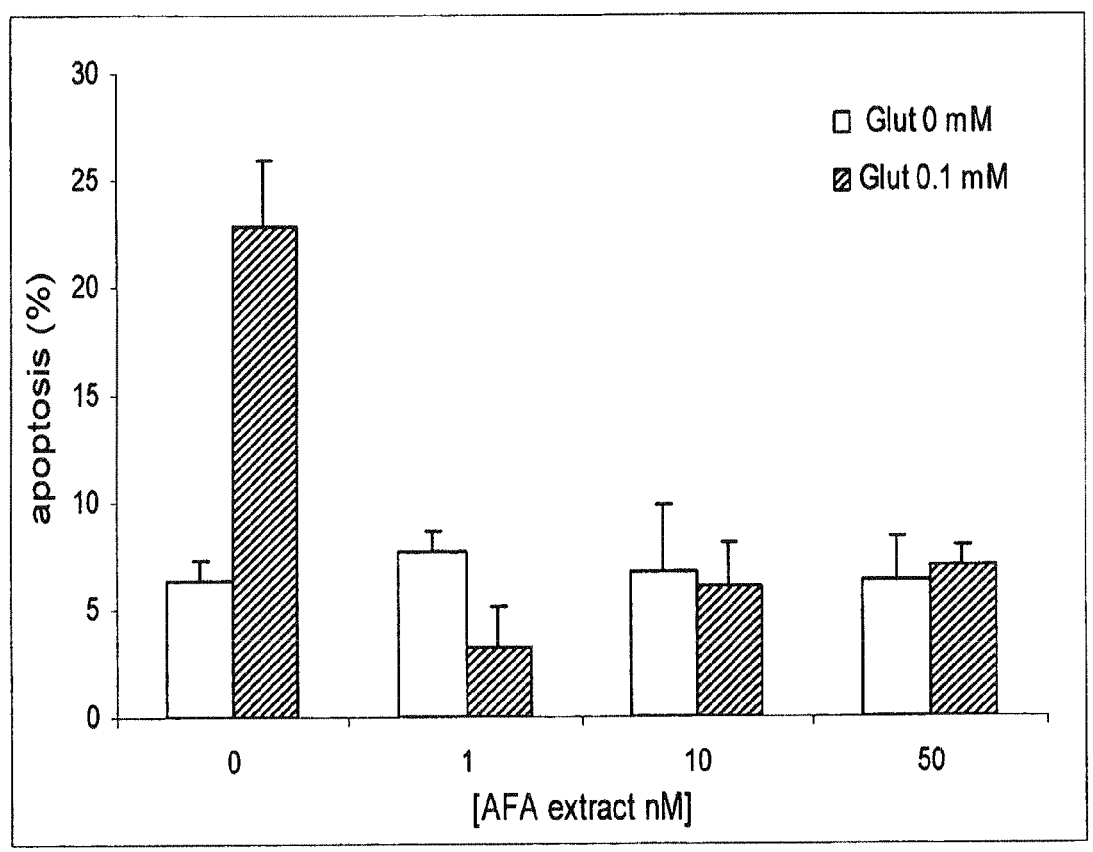
FIG. 18 shows the % apoptosis of an AFA extract with added glutamate.
Figure 19:
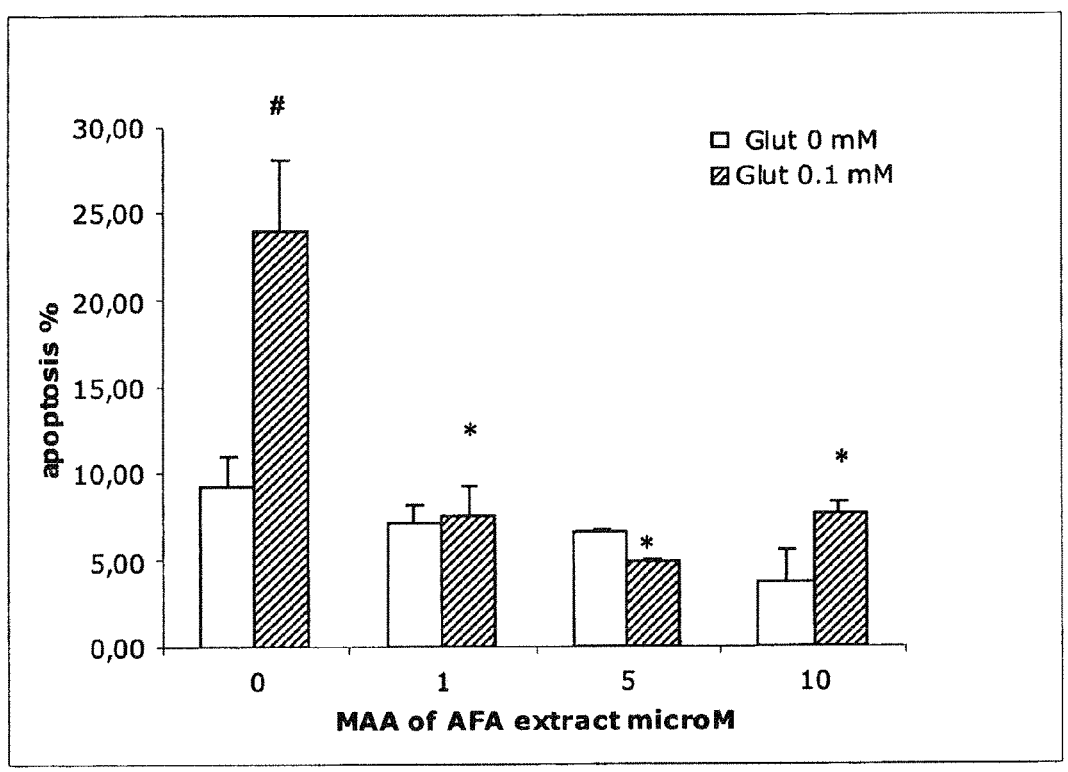
FIG. 19 shows the % apoptosis of MAAs from an AFA extract with added glutamate.

Through this glutamate damage test we have shown for the first time the neuroprotective ability of AFA Basic Extract, AFA-PC, its PCB and MAAs. As shown by FIG. 18, the addition of glutamate to the cultured neuron cells has increased the level of apoptosis to a percentage of 22.9%±3 n=4 (p<0.05); while the simultaneous addition of the AFA Basic Extract has generated a very high protection against glutamate toxicity, lowering the level of apoptosis below the control level of (6.3%±1 p>0.05) already with as low an amount of extract as 1 nM (results are means±SEM from 3 to 8 different cell cultures. # Significantly different when compared with control group (p<0.05); * Significantly different when compared with the glutamate control (p<0.05). As to the protection afforded by MAAs, they also lower the level of apoptosis below the control level, with the higher dosage of 1 µM (FIG. 19) results are means±SEM from 3 to 8 different cell cultures. # Significantly different when compared with control group (p<0.05); * Significantly different when compared with the glutamate control (p<0.05).).

Figure 20:
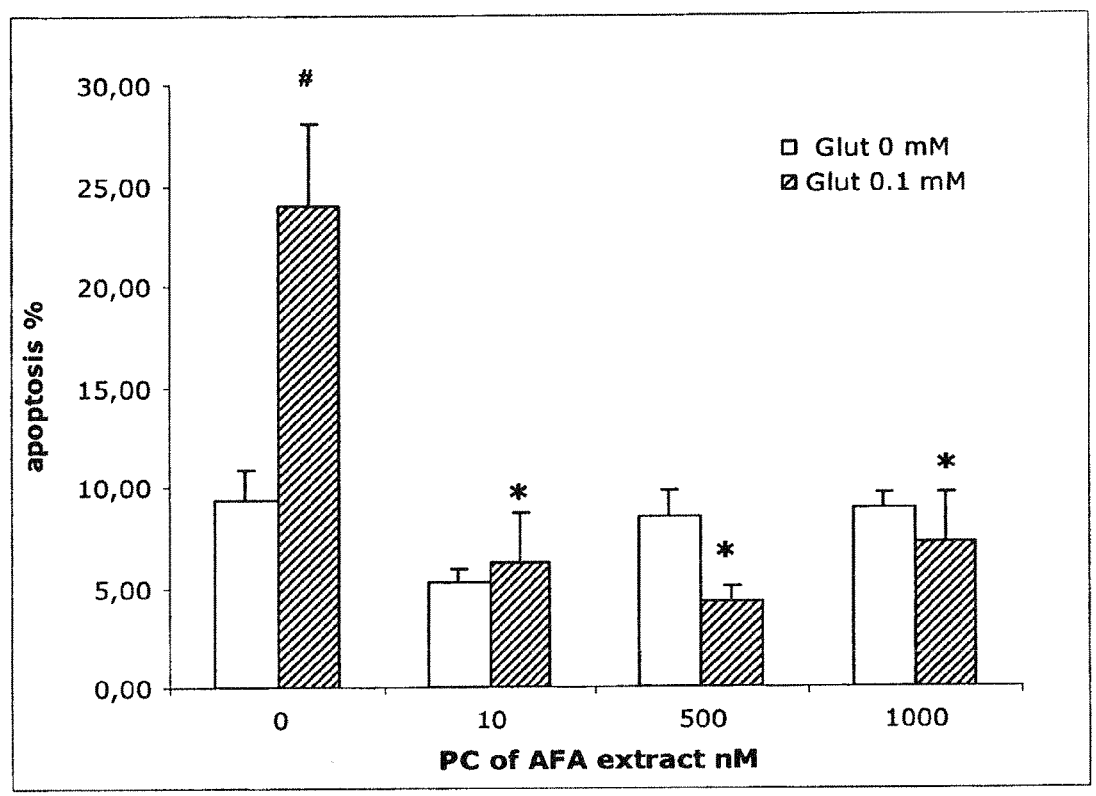
FIG. 20 shows the % apoptosis of phytochrome (PC) from an AFA extract with added glutamate.
Figure 21:
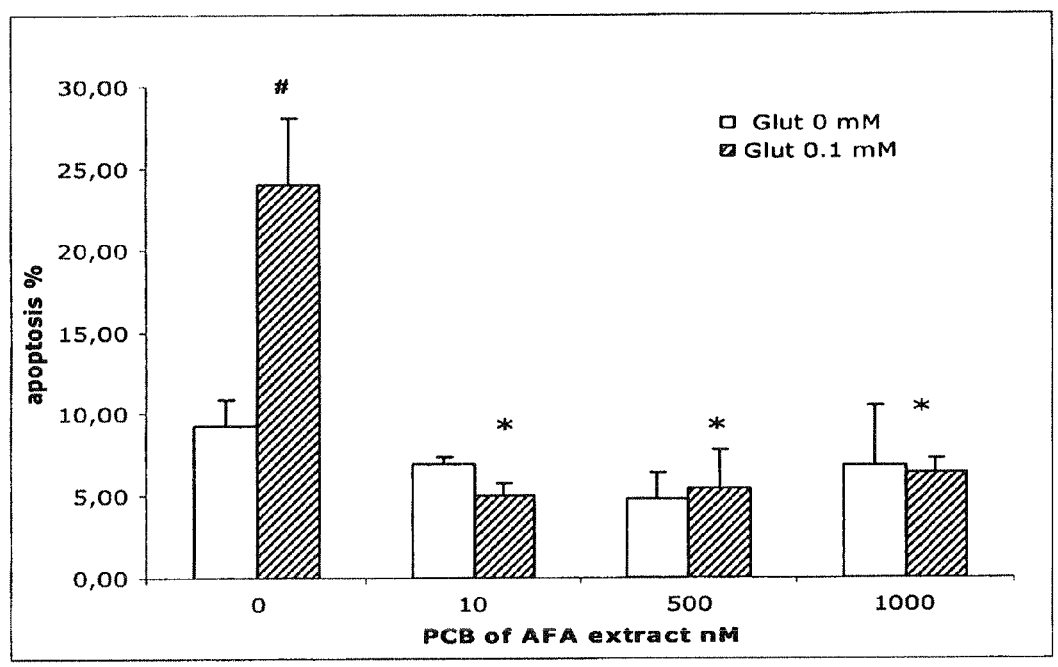
FIG. 21 shows the % apoptosis of chromophore phycocyanobilin (PCB) from an AFA extract with added glutamate.

Regarding AFA-PC and PCB, we see that their inhibition of apoptosis is very similar: their addition to the cell culture lowers the degree of apoptosis below the control with a dosage of approximately 10 nM (FIGS. 20 and 21—results are means±SEM from 3 to 8 different cell cultures. # Significantly different when compared with control group (p<0.05); * Significantly different when compared with the glutamate control (p<0.05)).

The degree of inhibition of AFA-PC is approximately equal to that of PCB. This is somewhat surprising, given that the PCB, supposedly its most active principle, once purified and thus more concentrated, should be significantly stronger than the whole molecule of which is the active component. The fact that it has practically the same potency means that in the whole PC there are other factors that may actually be even more potent than the PCB itself. We know that the whole PC is composed, besides C-PC and its PCB chromophore, of PEC, which includes as its chromophores both PCB and PVB (phycoviolobilin). Therefore, we can here assume that the factor that create a significant difference in potency between the purified PCB and the whole PC is precisely the PEC component, particularly its PVB chromophore, which is assumed to be a very strong antioxidant.

In terms of neuroprotection, MAAs seem to play a role, but significantly less than PC and PCB. However, the most powerful neuroprotectant is clearly the whole AFA extract, which is able to completely inhibit cell apoptosis at just 1 nM (nanomolar). This is 10 times the potency of PC and PCB. This can certainly be explained with the synergy of many different antioxidant factors present in the whole AFA extract; yet, since we have seen above that the AFA-phytochrome is possibly the most powerful antioxidant to date, being able to almost completely inhibit MDA (a late by-product of lipid-peroxidation) formation with just 16 nanomolars, it is very likely that AFA-phytochrome is the more important factor in explaining the higher potency of the Basic Extract. We can thus conclude that AFA-phytochrome, as well as any and all phytochromes, are important neuroprotective agents.

BIBLIOGRAPHY

1. Zhou G. et al., *Platelet monoamine oxidase B and plasma β-phenylethylamine in Parkinson's disease*, in *J Neurol Neurosurg Psychiatry*, 2001; 70:229-231, 229.
2. Ispida K. et al., *β-phenylethylamine stimulates striatal acetylcholine release through activation of the AMPA glutamatergic pathway*, in *Biol Pharm Bull* 2005 September; 28(9):1626-9.
3. Barroso N., Rodriguez M., *Action of β-phenylethylamine and related amines on nigrostriatal dopamine neurotransmission*, in *European Journal of Pharmacology*, 297 (1996), 195-203, 200.
4. Dyck L. E., *Release of monoamines from striatal slices by phenelzine and β-phenylethylamine*, in *Prog Neuropsychopharmacol Biol Psychiatry*, 1983, 7:797-800; Philips S. R., Robson A. M., *In vivo release of endogenous dopamine from rat caudate nucleus by phenylethylamine*, in *Neuropharmacology* 1983, 22:1297-1301; Raitieri m., et al., *Effect of sympathomimetic amines on the synaptosomal transport of noradrenaline, dopamine and 5-hydroxytryptamine*, in *Eur J Pharmacol* 1977, 41:133-143.

5. Janssen P. A. J, et al., *Does phenylethylamine act as an endogenous amphetamine in some patients?*, in *International Journal of Neuropsychopharmacology* 1999, 2: 229-240, 232.

6. Paterson I. A. et al., *2-phenylethylamine: a modulator of catecholamine transmission in the mammalian central nervous system?*, in *Journal of Neurochemistry* (1990), 55:1827-1837.

7. Sabelli H. C., Javaid I. J., *Phenylethylamine Modulation of Affect: Therapeutic and Diagnostic Implications*, in *Journal of Neuropsychiatry* (1995), 7(1):6-14, 7.

8. Mauro Federici et al., *Trace Amines Depress Gabab Response In Dopaminergic Neurons By Inhibiting Girk Channels*, in *Molecular Pharmacology* Fast Forward. Published on Jan. 11, 2005 as doi: 10.1124/mol. 104.007427.

9. Gusovsky F. et al., *A high pressure liquid chromatography method for plasma phenylacetic acid, a putative marker for depressive disorders*, in *Anal Biochem,* 1985 Feb. 15; 145(1):101-5. In this study, the depressed patients had a PAA level in the plasma of 327.64+/−45.44 ng/ml, against the 536.18+/−54.99 ng/ml. of the control group. In another study, in the urine of the depressed patients was found and average PAA of 66+/−23 mg/die, against the 104+/−23 mg/die of non depressed patients. See Sabelli H C. et al., *Urinary phenylacetic acid in panic disorder with and without depression*, in *Acta Psychiatr Scand* 1990 July; 82(1):14-6.

10. Szabo A. et al., *Phenylethylamine, a possible link to the antidepressant effects of exercise?*, in *Br J Sports Med* 2001 October; 35(5):342-3.

11. Sabelli H et al., *Sustained antidepressant effect of PEA replacement*, in *J Neuropsychiatry Clin Neurosci,* 8(2): 168-71.

12. Miura Y., *Plasma beta-phenylethylamine in Parkinson's disease*, in Kurume Med J 2000; 47(4):267-72.

13. Ibid.,

14. Ebadi M. et al., *Neuroprotective actions of selegiline*, in *J Neurosci Res* 2002 Feb. 1; 67(3):285-289.

15. Kemppainen N. et al., *Different pattern of reduction of striatal dopamine reuptake sites in Alzheimer's disease and ageing*, in *J Neural Transm* 2001; 108(7):827-36.

16. Knoll J., *(-)Deprenyl (Selegiline): past, present and future*, in *Neurobiology* (Bp) 2000; 8(2): 179-99.

17. Knoll J., *The pharmacological basis of the beneficial effects of (-)deprenyl (selegiline) in Parkinson's and Alzheimer's diseases*, in *J Neural Transm Suppl* 1993; 40:69-91.

18. Rimbau V., et al., *Protective effects of C-phycocyanin against kainic acid-induced neuronal damage in rat hippocampus*, in *Neurosci Lett* 1999 Dec. 3; 276(2):75-8. In this study phycocyanins have been used from the microalga *Spirulina*. The phycocyanins from Klamath algae are different and endowed with a higher antioxidant activity. See Benedetti S., Scoglio S., Canestrari F., et al., *Antioxidant properties of a novel phycocyanin extract from the blue-green alga Aphanizomenon Flos Aquae*, in *Life Sciences,* 75 (2004): 2353-2362.

19. Swanson J. et al., *Cognitive neuroscience of attention deficit hyperactivity disorder and hyperkinetic disorder*, in *Curr Opin Neurobiol.* 1998 April; 8(2):263-71.

20. Citazione solo di Benedetti et al. LifeScience; o menzione del parallelo brevetto? Attendere l'anno provisional in attesa di effettuare studi sulla neuroprotezione?

21. Kusaga A., *Decreased beta-phenylethylamine in urine of children with attention deficit hyperactivity disorder and autistic disorder*, in *No To Hattatsu* 2002 May; 34(3): 243-8; Matsuishi T, Yamashita Y., *Neurochemical and neurotransmitter studies in patients with learning disabilities*, in *No To Hattatsu* 1999 May; 31(3):245-8.

22. Kusaga A. et al., *Increased urine phenylethylamine after methylphenidate treatment in children with ADHD*, in *Ann Neurol* 2002 September; 52(3):372-4.

23. Jain A K., Et al., *Bupropion SR vs. placebo for weight loss in obese patients with depressive symptoms*, in *Obes Res.* 2002 October; 10(10):1049-56.

24. Rudolph et al., *A randomized, placebo-controlled, dose-response trial of venlafaxine hydrochloride in the treatment of major depression*, in *J Clin Psychiatry*(1998); 59(3):116-22.

25. PEA is a lipid-soluble molecule quite subject to be damaged by heat. This means that drying methods using high temperatures, such a freeze drying, usually have lower concentration of PEA. The highest content of PEA is found in the algae dried with the Refractance Window® method. It is from this type of algae that the Basic Extract is realized.

26. Yamada M. et al., *Clinical Pharmacology of MAO Inhibitors: Safety and Future*, in *Neurotoxicology* 2004; 25:215-21; Youdim M., et al., *Therapeutic Applications of Selective and Non-Selective Inhibitors of Monoamine Oxidase A and B that do not Cause Significant Tyramine Potentiation*, in *Neurotoxicology* 2004; 25:243-50.

27. Groniger A et al., *Photoprotective compounds in cyanobacteria, phytoplankton and macroalgae-a database*, in *J Photochem Photobiol B.* 2000 November; 58(2-3):115-22.

28. Suh H J et al., *Mycosporine glycine protects biological systems against photodynamic damage by quenching singlet oxygen with a high efficiency*, in *Photochem Photobiol.* 2003 August; 78(2):109-13.

29. Groniger A et al., *Photoprotective compounds in cyanobacteria, phytoplankton and macroalgae-a database*, in *J Photochem Photobiol B.* 2000 November; 58(2-3):115-22.

30. Sinha R P et al., *Induction of mycosporine-like amino acids (MAAs) in cyanobacteria by solar ultraviolet-B radiation*, in *J Photochem Photobiol B.* 2001 July; 60(2-3):129-35.

31. Garcia-Pichel F et al., *Occurrence of UV-Absorbing, Mycosporine-Like Compounds among Cyanobacterial Isolates and an Estimate of Their Screening Capacity*, in *Appl Environ Microbiol.* 1993 January; 59(1):163-169.

32. Glazer A. N., *Phycobiliproteins*, in *Methods Enzymol,* 1988, 167: 291-303.

33. Bhat V. B., et al., *C-phycocyanin: a potent peroxyl radical scavenger in vivo and in vitro*, in *Biochem Biophys Res Commun.,* 2000; 275(1):20-25; Romay, C. et al., *Antioxidant and antinflammatory properties of C-phycocyanin from blue-green algae*, in *Inflamm Res,* 1998, January; 47(1): 36-41.

34. Reddy C. M., et al., *Selective Inhibition of cyclooxygenase-2 by C-phycocyanin*, in *Biochem Biophys Res Commun.* 2000; 277(3): 599-603.

35. Gonzales R., et al., *Anti-inflammatory activity of phycocyanin extract in acetic acid induced colitis in rats*, in *Pharmacol Res,* 1999; 39(1): 55-9.

36. Gonzales R., et al., *Anti-inflammatory activity of phycocyanin extract in acetic acid induced colitis in rats*, in *Pharmacol Res,* 1999; 39(1): 55-9.

37. Vadiraja B B. et al., *Hepatoprotective effect of C-phycocyanin: protection for carbon tetrachloride and R-(+)-pulegone-mediated hepatotoxicty in rats*, in *Biochem Biophys Res Commun*, 1998; 249(2):428-31.
38. Romay C., et al., *Phycocyanin extract reduces leukotriene B4 levels in arachidonic induced mouse-ear inflammation test*, in *J Pharm Pharmacol*. 1999, 51(5):641-42. Come è noto, ii leucotriene B4 è uno dei fattori principalmente responsabili di patologie respiratorie quali asma e allergie.
39. Rimbau V., et al., *Protective effects of C-phycocyanin against kainic acid-induced neuronal damage in rat hippocampus*, in *Neurosci Lett* 1999, 276(2):75-8.
40. Rimbau V. et al., *C-phycocyanin protects cerebellar granule cells from low potassium/serum deprivation-induced apoptosis*, in *Naunyn Schmiedebergs Arch Pharmacol* 2001; 364(2): 96-104.
41. Glazer A. N., *Phycobilisomes*, in *Methods Enzymol* 1988, 167; 304-312.
42. Hirata T., et al., *Antioxidant activities of phycocyanobilin prepared from Spirulina platensis*, in *J Appl Phycol* 2000, 12:435-439.
43. Fuglistaller P., et al., *Isolation and characterization of phycoerythrocyanin and chromatic adaptation of the thermophilic cyanobacterium Mastigocladus laminosus*, in *Arch Microbiol* 1981, 129:268-274.
44. Rimbau V., et al., *Protective effects of C-phycocyanin against kainic acid-induced neuronal damage in rat hippocampus*, in *Neurosci Lett* 1999, 276(2):75-8.
45. The data in this table are drawn from the following studies: Magyar K. et al., *Pharmacological aspects of (−)-deprenyl*, in *Curr Med Chem*, 2004 August, 11(15): 2017-31; Hou et al., *Monoamine oxidase B (MAO-B) inhibition by active principles from Uncaria rhyncophylla*, in *Journal of Ethnopharmacology* 100 (2005) 216-220; Herraiz T, Chaparro C., *Human monoamine oxidase is inhibited by tobacco smoke: β-carboline alkaloids act as potent and reversible inhibitors*, in *Biochemical and Biophysical Research Communications* 326 (2005) 378-386; Kong L D et al., *Inihibition MAO-A and B by some plant-derived alkaloids, phenols and anthraquinones*, in *Journal of Ethnopharmacology* 91 (2004) 351-355.
46. Yoshida S. et al., *Fluorinated phenylcyclopropylamines. Part 3: Inhibition of monoamine oxidase A and B*, in *Bioorganic & Medicinal Chemistry* 12 (2004) 2645-2652.
47. Torres A. et al., *Porphyra-334, a potential natural source for UVA protective sunscreens*, in *Photochem. Photobiol. Sci.* 5 (2006) 432-435.
48. Hughes J, Lamparter T., *Prokaryotes and Phytochrome. The Connection to Chromophores and Signaling*, in *Plant Physiology*, December 1999, Vol. 121, pp. 1059-1068.
49. Garthwaite et al., *Endothelium-derived relaxing factor release on activation of NMDA receptors suggests role as intercellular messenger in the brain*, in *Nature*. 1988 Nov. 24; 336(6197):385-8.
50. Delgado-Esteban M. et al., *D-Glucose prevents glutathione oxidation and mitochondrial damage after glutamate receptor stimulation in rat cortical primary neurone*, in *J Neurochem*. 2000 October; 75(4):1618-24.

The invention claimed is:

1. A method of treating Alzheimer's disease comprising the steps of:
    administering to a subject in need thereof, an extract of microalga *Aphanizomenon Flos Aquae* Aquae Ralfs ex Born. & Rah. Var. *flos aquae* (AFA Klamath) comprising phenylethylamine and a component selected from the group consisting of: C-Phycocyanin (C-PC), phycoerythrocyanin (PEC), a C-Phycocyanin/phycoerythrocyanins complex (C-PC/PEC), phycoviolobilin (PVB), AFA-phytochrome, chromophore phycocyanobilin (PCB), mycosporine-like amino acids (MAAs), and a mixture thereof, wherein the extract is prepared by:
    diluting dried AFA Klamath powder with water to form a mixture;
    sonicating the mixture;
    centrifuging the sonicated mixture to form a supernatant;
    collecting the supernatant, wherein the supernatant is the extract; and
    purifying by passing the extract through an ultrafiltration system having a molecular weight cut-off of 30,000 Dalton to provide the extract for administering to the subject in need thereof for Alzheimer's disease.

2. The method of claim 1, wherein the extract comprises the phenylethylamine at about 0.1 to 100 mg, the AFA-phytochrome at about 0.1 to 1,000 mg, the MAAs at about 0.1 to 1,000 mg, and the C-PC and PEC combined at about 1 to 2,500 mg.

3. A method of treating Alzheimer's disease, the treatment comprising the steps of:
    administering to a subject in need of treatment thereof, an extract of microalga *Aphanizomenon Flos Aquae* Aquae Ralfs ex Born. & Rah. Var. *flos aquae* (AFA Klamath) comprising phenylethylamine and a component selected from the group consisting of: C-Phycocyanin (C-PC), phycoerythrocyanin (PEC), a C-Phycocyanin/phycoerythrocyanins complex (C-PC/PEC), phycoviolobilin (PVB), AFA-phytochrome, chromophore phycocyanobilin (PCB), mycosporine-like amino acids (MAAs), and a mixture thereof, wherein the extract is prepared by:
    freezing freshly harvested AFA Klamath algae;
    thawing the algae;
    centrifuging the thawed algae to form a supernatant;
    collecting the supernatant, wherein the supernatant is the extract; and
    purifying by passing the extract through an ultrafiltration system having a molecular weight cut-off of 30,000 Dalton.

4. The method of claim 3, wherein the extract comprises the phenylethylamine at about 0.1 to 100 mg, the AFA-phytochrome at about 0.1 to 1,000 mg, the MAAs at about 0.1 to 1,000 mg, and the C-PC and PEC combined at about 1 to 2,500 mg.

5. A method of treating a neurological disease, condition, dysfunction or disorder selected from the group consisting of Alzheimer's disease depression, and mood disturbances, the treatment comprising the steps of:
    administering to a subject in need thereof, an extract of microalga *Aphanizomenon Flos Aquae* Aquae Ralfs ex Born. & Rah. Var. *flos aquae* (AFA Klamath) comprising phenylethylamine and a component selected from the group consisting of: C-Phycocyanin (C-PC), phycoerythrocyanin (PEC), a C-Phycocyanin/phycoerythrocyanins complex (C-PC/PEC), phycoviolobilin (PVB), AFA-phytochrome, chromophore phycocyanobilin (PCB), mycosporine-like amino acids (MAAs), and a mixture thereof, wherein the extract is prepared by:
    diluting dried AFA Klamath powder with water to form a mixture;

sonicating the mixture;
centrifuging the sonicated mixture to form a supernatant;
collecting the supernatant, wherein the supernatant is the extract, and the extract comprises the phenylethylamine at about 0.1 to 100 mg, the AFA-phytochrome at about 0.1 to 1,000 mg, the MAAs at about 0.1 to 1,000 mg, and the C-PC and PEC combined at about 1 to 2,500 mg; and
purifying by passing the extract through an ultrafiltration system having a molecular weight cut-off of 30,000 Dalton to provide the extract for administering to the subject in need thereof for Alzheimer's disease, depression, and mood disturbances.

6. method of treating a neurological disease, condition, dysfunction or disorder selected from the group consisting of Alzheimer's disease depression, and mood disturbances, the treatment comprising the steps of:
administering to a subject in need thereof, an extract of microalga *Aphanizomenon Flos Aquae* Aquae Ralfs ex Born. & Rah. Var. *flos aquae* (AFA Klamath) comprising phenylethylamine and a component selected from the group consisting of: C-Phycocyanin (C-PC), phycoerythrocyanin (PEC), a C-Phycocyanin/phycoerythrocyanins complex (C-PC/PEC), phycoviolobilin (PVB), AFA-phytochrome, chromophore phycocyanobilin (PCB), mycosporine-like amino acids (MAAs), and a mixture thereof, wherein the extract is prepared by:
freezing freshly harvested AFA Klamath algae;
thawing the algae;
centrifuging the thawed algae to form a supernatant;
collecting the supernatant, wherein the supernatant is the extract, and the extract comprises the phenylethylamine at about 0.1 to 100 mg, the AFA-phytochrome at about 0.1 to 1,000 mg, the MAAs at about 0.1 to 1,000 mg, and the C-PC and PEC combined at about 1 to 2,500 mg; and
purifying by passing the extract through an ultrafiltration system having a molecular weight cut-off of 30,000 Dalton to provide the extract for administering to the subject in need thereof for Alzheimer's disease, depression, and mood disturbances.

* * * * *